United States Patent
Lai

(10) Patent No.: US 10,221,458 B2
(45) Date of Patent: Mar. 5, 2019

(54) METHOD FOR SCREENING CANCER

(75) Inventor: Hungcheng Lai, Taipei (TW)

(73) Assignee: NATIONAL DEFENSE MEDICAL CENTER, Taipei (TW)

( * ) Notice: Subject to any disclaimer, the term of this patent is extended or adjusted under 35 U.S.C. 154(b) by 481 days.

(21) Appl. No.: 14/424,876

(22) PCT Filed: Aug. 31, 2012

(86) PCT No.: PCT/CN2012/001211
§ 371 (c)(1),
(2), (4) Date: Sep. 3, 2015

(87) PCT Pub. No.: WO2014/032205
PCT Pub. Date: Mar. 6, 2014

(65) Prior Publication Data
US 2015/0361502 A1    Dec. 17, 2015

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 2009/0004660 A1 | 1/2009 | Inazawa et al. | |
| 2010/0273151 A1 | 10/2010 | Tapscott et al. | |
| 2011/0027796 A1* | 2/2011 | An | C12Q 1/6886 435/6.11 |
| 2011/0160091 A1* | 6/2011 | Dietrich | C12Q 1/6886 506/16 |
| 2011/0300536 A1* | 12/2011 | Li | C12Q 1/6886 435/6.11 |
| 2011/0301050 A1 | 12/2011 | Pfeifer et al. | |
| 2012/0196756 A1* | 8/2012 | Ahlquist | C12Q 1/6827 506/2 |
| 2013/0041047 A1 | 2/2013 | Orntoft et al. | |

FOREIGN PATENT DOCUMENTS

| | | |
|---|---|---|
| JP | 2011-160711 | 8/2011 |
| JP | 2011160711 | 8/2011 |
| JP | 2012-44924 | 3/2012 |
| WO | WO2008084219 | 7/2008 |
| WO | WO2009105549 | 8/2009 |
| WO | WO2009115615 | 9/2009 |
| WO | WO2010007083 | 1/2010 |
| WO | WO2010007083 A2 | 1/2010 |
| WO | WO 2012031329 | 3/2012 |
| WO | WO2012031329 | 3/2012 |
| WO | WO2012104642 | 8/2012 |
| WO | WO2012174256 | 12/2012 |
| WO | WO2013033333 | 3/2013 |
| WO | 2014032205 A1 | 3/2014 |

OTHER PUBLICATIONS

Wu et al. (Cancer Res; 70(7); 2718-27). (Year: 2010).*
Eijsink et al. Int. J. Cancer: 130, 1861-1869 (2012) (Year: 2012).*
Zhuang et al.PLOS Genetics Feb. 2012 l vol. 8 l Issue 2 l e1002517, 13 pages (Year: 2012).*
NCBI GEO database accession GSE30760, including POU4F3 (cg18482268) data. obtained from https://www.ncbi.nlm.nih.gov/geo/geo2r/?acc=GSE30760. publicly available Feb. 20, 2012. 3 pages. (Year: 2012).*
Schlesinger et al. vol. 39 No. 2 Feb. 2007 Nature Genetics, pp. 232-236 (Year: 2007).*
European Search report dated Oct. 10, 2016 for European Patent Application No. 12883916.4.
Gregory A Michelotti et al., Epigenetic regulation of human alpha-l6-adrenergc receptor gene expression: a role for DNA methylation in Sp I-dependent regulation, The FASEB Journal, vol. 21, No. 9, Jan. 1, 1979, pp. 1979-1993.
Mary L. Garcia-Cazarin et al., The a1D-Adrenergic Receptor Induces Vascular Smooth Muscle Apoptosis via a ps3-Dependent Mechanism, Molecular Pharmacology, vol. 74, No. 4, Jan. 1, 2008, pp. 1000-1007.
Xiwei Wu et al., CpG Island Hypermethylation in Human Astrocytomas, Cancer Research, vol. 70, No. 7, Mar. 16, 2010, pp. 2718-2727.
Russian office action dated Jun. 20, 2016 for the Russian counterpart Patent Application No. 2015111627.
Narayan Shivapurkar et al., Evaluation of Candidate Methylation Markers to Detect Cervical Neoplasia, Gynecologic Oncology, 2007, No. 107, pp. 549-553.
Yan Jia et al., SOX17 antagonizes WNT/β-catenin signaling pathway in hepatocellular carcinoma, Epigenetics, 2010, vol. 5, No. 8. pp. 743-749.
English translation of JP2011160711.
English abstract of JP2011160711.
WO2014032205A1 is the international publication of PCT/CN2012/001211.
Translation of the bibliography page of International publication WO2014032205A1.
International Search Report of PCT/CN2012/001211.
Office action dated Jun. 22, 2017 for the New Zealand counterpart application No. 705485.
Lim et al., "Cervical dysplasia: Assessing methylation status (Methylight) of CCNA1, DAPK1, HS3ST2, PAX1 and TFPI2 to improve diagnostic accuracy," Gynecologic Oncology, vol. 119 (2010) 225-231.

(Continued)

*Primary Examiner* — Juliet C Switzer
(74) *Attorney, Agent, or Firm* — WPAT, P.C., Intellectual Property Attorneys; Anthony King

(57) ABSTRACT

Disclosed in the present invention is a method for screening cancer, comprising the following steps: (1) providing a specimen to be detected; (2) detecting the methylation status of CpG sequence of at least one target gene which is at least one of ADRA1D, AJAP1, HS3ST2, MAGI2, POU4F2, POU4F3, PTGDR, SOX17 and SYT9 in genomic DNA of the specimen; (3) determining whether cancer or precancerous lesions are present in the specimen according to the methylation status of at least one target gene.

23 Claims, 9 Drawing Sheets
Specification includes a Sequence Listing.

(56) References Cited

OTHER PUBLICATIONS

Van Der Meide et al., "Promoter methylation analysis of WNT/β-catenin signaling pathway regulators to detect adenocarcinoma or its precursor lesion of the cervix," Gynecologic Oncology, vol. 123 (2011) 116-122.
Fu et al., "Sox17, the canonical Wnt antagonist, is epigenetically inactivated by promoter methylation in human breast cancer," Breast Cancer Research and Treatment, vol. 119(3), Mar. 2009, pp. 601-612.
Office action dated Jun. 21, 2016 for the Japanese counterpart application 2015-528825.
English abstract translation of the office action dated Jun. 21, 2016 for the Japanese counterpart application 2015-528825.
Database Genbank [online], Accession No. EU326302, Feb. 20, 2008 uploaded, Homo sapiens adrenergic, alpha1D, receptor (ADRA1D) gene, complete cds, Feb. 20, 2008.
Office action dated Jan. 16, 2017 for the Japanese counterpart application No. 2015-528825.
English translation of the office action dated Jan. 16, 2017 for the Japanese counterpart application 2015-528825.
Office action dated Nov. 17, 2016 for the counterpart Ukraine Application No. a 2015 02917.
English translation of the office action dated Nov. 17, 2016 for the counterpart Ukraine Application No. a 2015 02917.
Narayan Shivapurkar et al., Evaluation of candidate methylation markers to detect cervical neoplasia, Gynecologic Oncology 107 (2007) 549-553.
Xiwei Wu et al., CpG Island Hypermethylation in Human Astrocytomas, Molecular and Cellular Pathobiology, Cancer Res; 70(7) Apr. 1, 2010.
Kazimierz O. Wrzeszczynski et al., Identification of Tumor Suppressors and Oncogenes from Genomic and Epigenetic Features in Ovarian Cancer, PLoS ONE, Dec. 2011, vol. 6, Issue 12.
Yan Jia et al., SOX17 antagonizes WNT/β-catenin signaling pathway in hepatocellular carcinoma. Epigenetics 5:8, 743-749; Nov. 16, 2010.

* cited by examiner

METHOD FOR SCREENING CANCER

FIELD OF THE INVENTION

The present invention relates to method III for screening cancer.

BACKGROUND OF THE INVENTION

Cervical cancer is one of the primary causes of death for women worldwide and in Taiwan. According to the statistics by the World Health Organization (WHO) in 2002, cervical cancer is the second cause of death for women cancers worldwide, only subsequent to breast cancer. Periodic cervical cancer screening is the best way of cervical cancer prevention. Currently, there are two methods for cervical cancer screening. One is the most commonly known Pap smear and the other is HPV testing. Pap smear is performed by obtaining the discharge from the cervical, and observing whether cancerous lesion occurs in the detached epithelial cells by microscopy for early-stage detection of cervical cancer. HPV testing is performed by using polymerase chain reaction (RT-PCR) or Hybrid Capture to examine whether human papilloma virus (HPV) is present in the sample.

However, because it requires physicians to obtain the sample and medical technologists/pathologists to interpret the data from of smear, in addition to high false negative rate and the subsequent delay in diagnosis and treatment of the precancerous lesion, the required quality in human resource and cost is overly high. For many developing countries, it is difficult to promote. On the other hand, although HPV testing is highly sensitive, it is also prone to high false positive rate. Not only the patient worries in vain, but also much medical resource wasted in the follow-up examinations of these false positive patients. Therefore, there remains a problem of how to elevate the accuracy and convenience of screening methods of cervical cancer for promoting cervical cancer screening.

Genomic deletions are considered an important factor in tumor formation. For a long time, we are used to the concept that the code of genes relies on the permutation and combination of the four bases. Early as in 1975, Knudson proposed the two-hit theory, pointing out that some mutations or deletions accompanying homologous tumor suppressor genes may cause or are prone to cause cancer. However, other information that affects phenotype may exist in the modified base, 5-methylcytosine. 5-methylcytosine is found to exist in the palindrome sequence 5'-CpG-3' in mammalian cells. In mammalian cells, besides the regions that are called "CpG islands (CGIs)," most CpG dinucleotide pairs are methylated. CpG islands refer to regions having about 1000 base pairs (1 Kb) that contain large amounts of GC- and CpG-. Usually, they are present around the genes, and are found near the promoters of broadly-expressed genes. Methylation of cytosine occurs after DNA synthesis, which transfers methyl group from the methyl group donor, S-adenosylmethionine (SAM), to the 5th carbon of cytosine. This enzymatic reaction is carried out by DNA methyltransferase (DNMTs). DNMT1 is the primary methyltransferase in mammals, which is responsible for the post-replicative restoration of hemi-methylated positions to full methylation, and thus maintenance of methylation. On the other hand, DNMT3A and DNMT3B are considered to be responsible for methylation of new positions, a process called de novo methylation.

Loss of methylation in CpG dinucleotide pairs refers to the generally-known low degree of methylation which is the first epigenetic abnormality in cancer cells. However, researches in past few years indicate that site-specific hypermethylation (such as in some tumor suppressor genes) is associated with loss of function. This may provide selective advantages during tumor formation. Hypermethylation of CpG islands in the promoter region may induce chromatin remodeling through gene silencing accompanied with histone modification. In addition to chromosome deletion and gene mutation, epigenetic silencing of tumor suppressor genes caused by hypermethylation of promoter is also common in human cancers.

Recent researches in epidemiology demonstrate that the concentration of serum folate (a primary source of methyl group) is associated with the infection and clearance of HPV. In the metabolism of methyl cycle, genetic polymorphisms of enzymes are also reported as associated with the development of cervical epithelial lesions. Like the concept of super gene evolution, researches on the association between DNA methylation and cervical cancer are also prevailing. Researches on DNA methylation of cervical cancer increase with time, indicating the possibility of using methylation for cervical cancer screening. Due to the interaction between genetics and the environment, the degree of methylation of tumor suppressor genes varies among different genes and different populations. Different diseases may have different methylator phenotypes. However, the methylator phenotype of cervical cancer and association with HPV are still unknown. What specific genes would be methylated in cervical cancer and how many genes is required to meet the need in clinical application remain the issues that need to be verified in the future.

Based on the above, the current methods of cervical cancer screening still have many defects and are not properly designed. An improvement is needed.

The inventors of the subject application have filed relevant patent applications in Taiwan (TW Pat. Pub. No. 200831900, TW Pat. Pyb. No. 201038739), China (CN Appl. No. 200810094659.2, CN Appl. No. 200910135501.X), Malaysia (UI20085354) and the USA (US Pat. Pub. No. 20080311570, US Pat. Pub. No. 20110045465) (hereafter refers to as the prior applications). The method III for screening cancer is an extension of the prior applications. The inventors of the subject application discovered novel biomarkers for cancer screening and the screening methods.

SUMMARY OF THE INVENTION

The purpose of present invention is to provide a method for screening cervical cancer for use as a first-line cervical cancer screen.

Another purpose of present invention is to provide a method for screening cervical cancer. The method not only can be used as a first-line cervical cancer screen but also can be used as a second-line cervical cancer screen to facilitate HPV testing or uncertain smear results so as to achieve more accurate cervical cancer screening results.

Still another purpose of present invention is to provide a method for screening cancer. In addition to applying to cervical cancer screening, the method can be used in the screening of other cancers (such as: ovarian cancer, liver cancer, colon cancer, breast cancer, oral cancer, endometrial cancer and sarcoma) to facilitate the determination on abnormal specimen.

A method of cancer screening to achieve the above purposes of the present invention is to detect the methylation status of target gene in the cells of a specimen to be detected.

The detection serves as a screening indicator of the presence or absence of cancer. The method comprises the following steps:

step 1: providing the specimen to be detected;

step 2: detecting the methylation status of CpG sequence of at least one target gene which is at least one of ADRA1D, AJAP1, HS3ST2, MAGI2, POU4F2, POU4F3, PTGDR, SOX17 and SYT9 in genomic DNA of the specimen; and step 3: determining whether cancer or precancerous lesions are present in the specimen according to the methylation status of the target gene, or utilizing the methylation status as an indicator of prognosis after treatment.

The specimen to be detected is Pap smear, ovarian cancer tissues, ascites, blood, urine, feces, phlegm, oral mucosal cells, gastric fluid, bile, cervical epithelial cells, or cancer tissues after surgery.

The method of detecting the methylation status of CpG sequence of target gene comprises, but is not limited to, methylation specific polymerase chain reaction (MSP), quantitative methylation specific polymerase chain reaction (QMSP), bisulfite sequencing (BS), microarrays, mass spectrometry, denaturing high performance liquid chromatography (DHPLC).

The target gene ADRA1D has the nucleotide sequence as set forth in SEQ ID NO: 1.

The target gene AJAP1 has the nucleotide sequence as set forth in SEQ ID NO: 2.

The target gene HS3ST2 has the nucleotide sequence as set forth in SEQ ID NO: 3.

The target gene MAGI2 has the nucleotide sequence as set forth in SEQ ID NO: 4.

The target gene POU4F2 has the nucleotide sequence as set forth in SEQ ID NO: 5.

The target gene POU4F3 has the nucleotide sequence as set forth in SEQ ID NO: 6.

The target gene PTGDR has the nucleotide sequence as set forth in SEQ ID NO: 7.

The target gene SOX17 has the nucleotide sequence as set forth in SEQ ID NO: 8.

The target gene SYT9 has the nucleotide sequence as set forth in SEQ ID NO: 9.

The methylation status of the target gene ADRA1D is detected by the primer pairs having the nucleotide sequences as set forth in SEQ ID NO: 10-11.

The methylation status of the target gene AJAP1 is detected by the primer pairs having the nucleotide sequences as set forth in SEQ ID NO: 12-13.

The methylation status of the target gene HS3ST2 is detected by the primer pairs having the nucleotide sequences as set forth in SEQ ID NO: 14-15.

The methylation status of the target gene MAGI2 is detected by the primer pairs having the nucleotide sequences as set forth in SEQ ID NO: 16-17.

The methylation status of the target gene POU4F2 is detected by the primer pairs having the nucleotide sequences as set forth in SEQ ID NO: 18-19.

The methylation status of the target gene POU4F3 is detected by the primer pairs having the nucleotide sequences as set forth in SEQ ID NO: 20-21.

The methylation status of the target gene PTGDR is detected by the primer pairs having the nucleotide sequences as set forth in SEQ ID NO: 22-23.

The methylation status of the target gene SOX17 is detected by the primer pairs having the nucleotide sequences as set forth in SEQ ID NO: 24-25.

The methylation status of the target gene SYT9 is detected by the primer pairs having the nucleotide sequences as set forth in SEQ ID NO: 26-27.

The primers comprise sequences having at least 80% sequence identity, complementarity or at least 10 contiguous nucleotides identical to the corresponding sequences.

In addition, the above screening markers and screening method can further be used in the screening of cervical cancer, ovarian cancer, liver cancer, colon cancer, breast cancer, oral cancer, endometrial cancer or sarcoma.

The term "specimen to be detected" refers to an in vitro sample to be detected. The sample includes the in vitro specimen sample of the above-mentioned Pap smear, ascites, blood, urine, feces, phlegm, oral mucosal cells, gastric fluid, bile, cervical epithelial cells, or cancer tissues after surgery. The cancer screening method of the present invention is used to detect the methylation status of target genes in the in vitro samples, and may serve as a screen indicator for various cancers. The cancer screening method and screening markers provided by the present invention can be used by screening researchers to perform screening in the laboratory.

The term "indicator gene" refers to the target gene in which CpG sequences are methylated. The methylation status of the target gene in the specimen cells to be detected is detected and used as a screening indicator of the presence or absence cancer.

The method of screening cancer provided by the present invention has the following advantages compared to the above-mentioned prior techniques:

1. The method of screening cancer provided by the present invention uses the degree of methylation of specific genes in the in vitro specimen as the screening indicator for the presence or absence of cancer. Compared to Pap smear or HPV testing, the sensitivity and specificity of the method of screening cancer of the present invention are both higher.

2. The method of screening cancer provided by the present invention, in addition to being applied on cervical cancer detection, can also be used in the screening of other cancers (such as: ovarian cancer, liver cancer, colon cancer, breast cancer, oral cancer, endometrial cancer and sarcoma) to facilitate the determination on abnormal specimen.

DETAILED DESCRIPTION OF THE INVENTION

Figure 1:
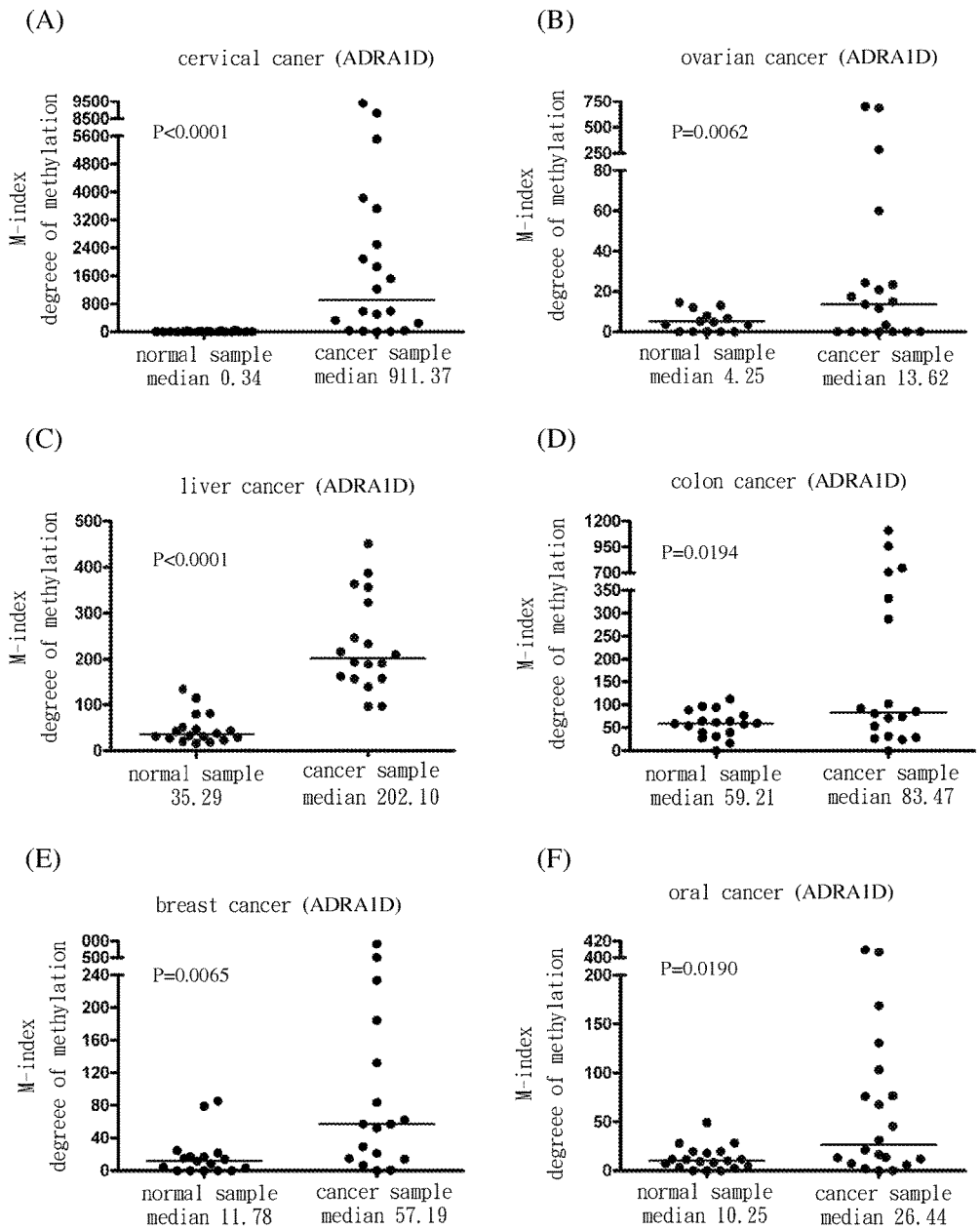
FIG. 1 shows the result of degree of methylation of the target gene ADRA1D used in the method of screening cancer of the present invention by bisulfite sequencing (BS) in various normal and cancerous tissue samples: (A) uterine cervix, (B) ovarian tumor, (C) liver, (D) colon, (E) breast, and (F) oral tissue.
Figure 2:
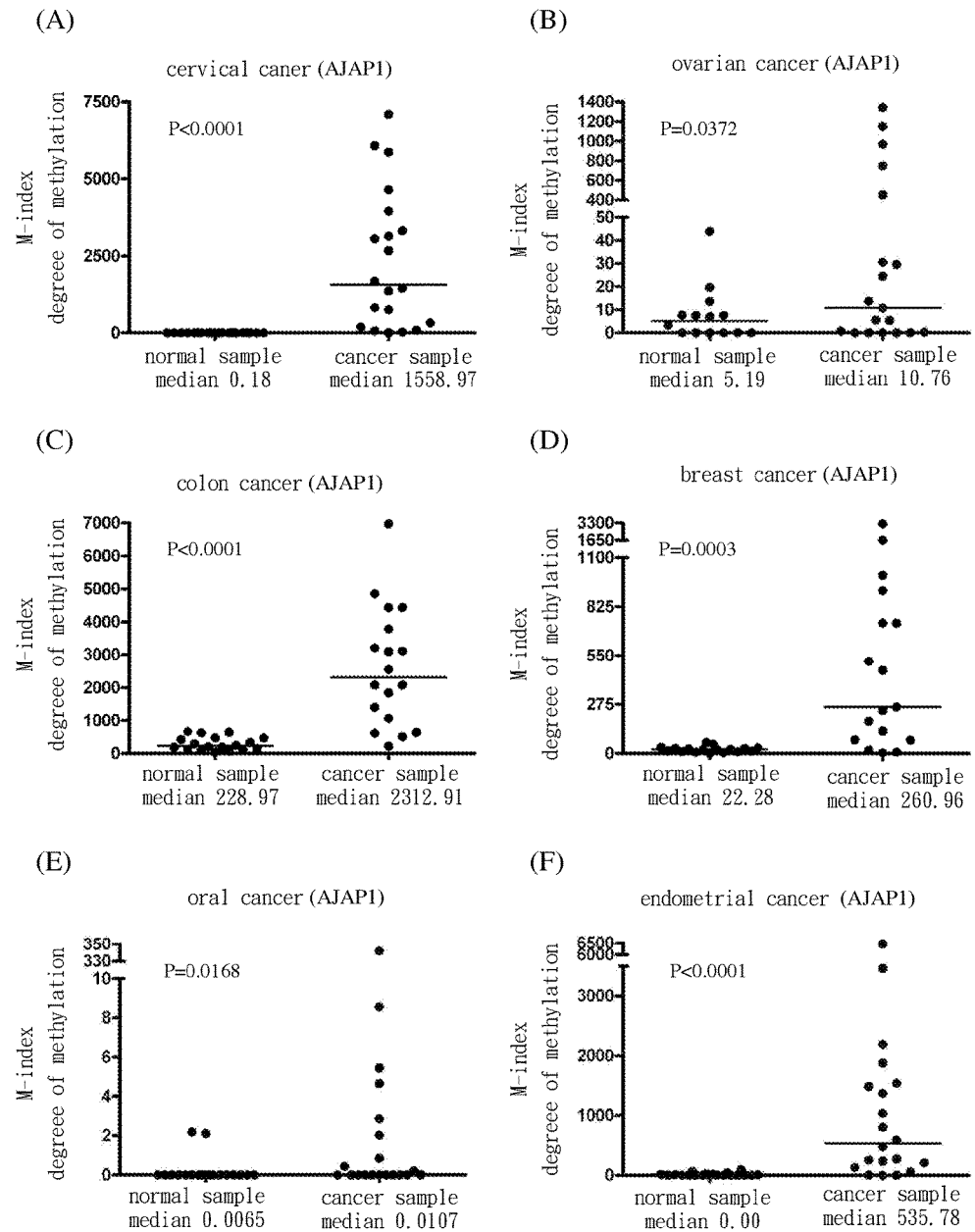
FIG. 2 shows the result of degree of methylation of the target gene AJAP1 used in the method of screening cancer of the present invention by bisulfite sequencing (BS) in various normal and cancerous tissue samples: (A) uterine cervix, (B) ovarian tumor, (C) colon, (D) breast, (E) oral tissue, and (F) endometrial tissue.
Figure 3:
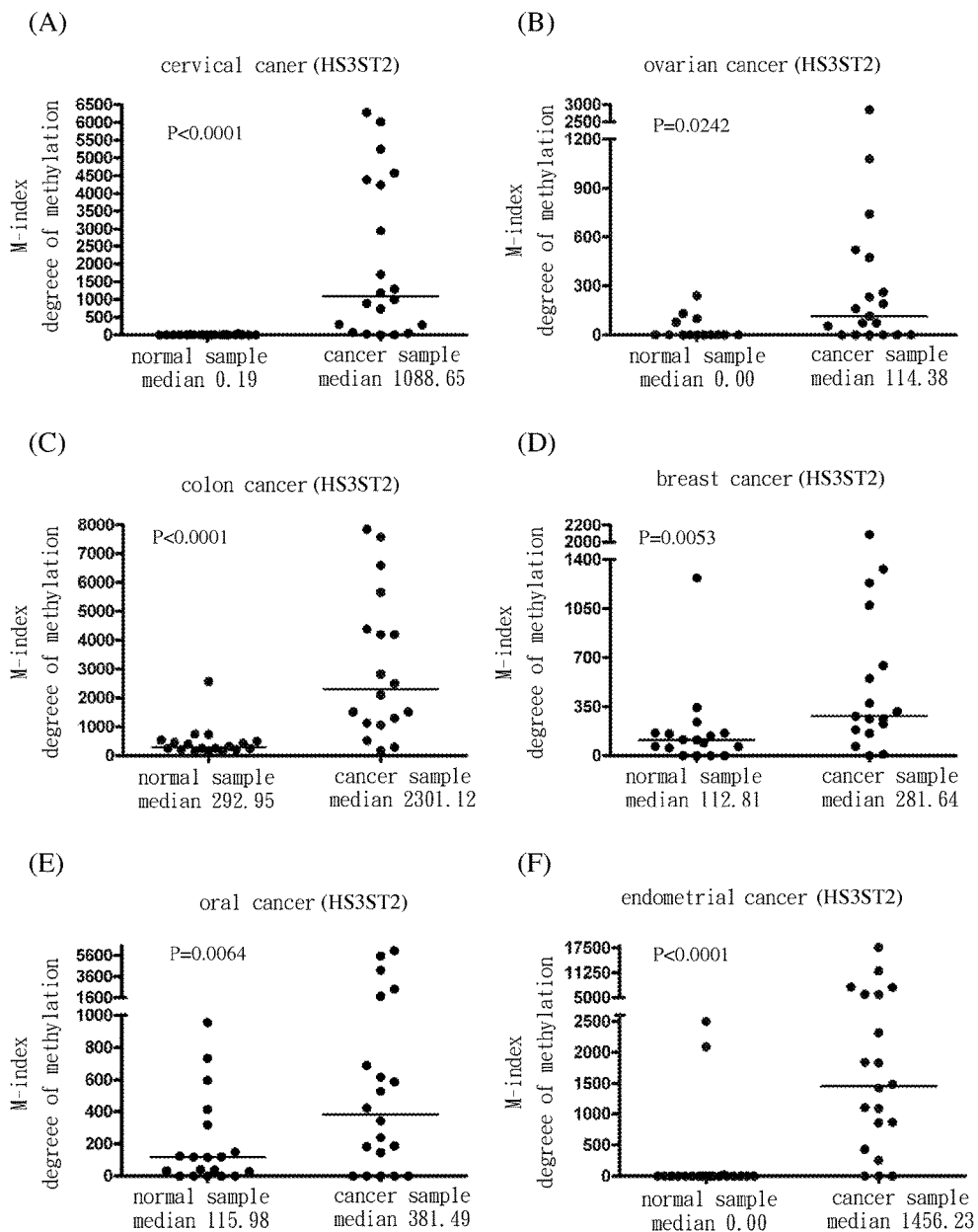
FIG. 3 shows the result of degree of methylation of the target gene HS3ST2 used in the method of screening cancer of the present invention by bisulfite sequencing (BS) in various normal and cancerous tissue samples: (A) uterine cervix, (B) ovarian tumor, (C) colon, (D) breast, (E) oral tissue, and (F) endometrial tissue.

The present invention will be further illustrated by the following examples. However, the examples are only for illustrative purpose and should not be construed as any limitation to the present invention.

Example 1: Materials and Methods

1. Materials

The tested materials comprise a series of intact cervical lesion samples, including: squamous cell carcinoma (SCC), adenocarcinoma (AC), and normal cervical samples. All the cervical samples (SCC+AC, n=20; normal, n=20), ovary samples (cancer of ovary, n=19; normal, n=14), colon samples (Ca of colon, n=18; normal, n=18), liver tissue samples (HCC, n=18; normal, n=18), oral samples (oral Ca, n=20; normal, n=19), endometrial cancer samples (endometrial Ca, n=20; normal, n=20), breast tissue samples (cancer of breast, n=17; normal, n=17), sarcoma samples (sarcoma, n=18; normal, n=16) are obtained from Tri-Service General Hospital in Taipei. The genomic DNA of each sample is extracted using QIAamp DNA kit followed by DNA modification kit (CpGenome™ DNA Modification Kit, Millipore, Temecula, Calif.) produced by Millipore to perform bisulfite modification for analysis of DNA methylation of the whole genome.

2. Analysis of DNA Methylation Using Whole Genomic Methylation Chip (Illuminea Infinium HumanMethylation27 BeadChip)

Extract DNA from cancer tissue samples and normal tissue samples, respectively. Subject the extracted DNA to bisulfite modification and then adjust the products to an equal concentration (ng/μl). Mix the cancer tissue sample DNA or normal tissue sample DNA having the same concentration into two samples for detection, and analyze the degree of methylation of the whole genome on Infinium HumanMethylation27 methylation chip (Illumina, San Diego, Calif.). The experimental steps are performed according to the manufacturer's instructions. Analyze the degree of methylation of genes on each chip using Illumina chip scanner (Bead Array reader) and GenomeStudio software (Illumina).

Infinium HumanMethylation27 methylation chip contains 14,475 genes and can detect the degree of methylation on 27,578 CpG sites in these genes. The analysis of degree of methylation on CpG sites is presented by "β values." The β value of each CpG site is between 0 and 1, where 0 represents no methylation and 1 represents 100% methylation.

3. Bisulfite Modification, Quantitative Methylation-Specific PCR (qMSP), and Pyrosequencing Use the DNA modification kit (CpGenome™ DNA Modification Kit, Millipore, Temecula, Calif.) produced by Millipore to perform bisulfite modification: obtain 1 μg sample genomic DNA and perform chemical modification to the genomic DNA using sodium bisulfite. In single chain DNA, all non-methylated cytosine will undergo deamination and be converted into uracil. Methylated cytosine will not be modified and will maintain the status of 5-methylcytosine. Finally, dissolve the sample DNA after reaction into 70 μl, 55° C. TE buffer for methylation specific quantitative PCR.

Use the normal DNA of human peripheral blood for bisulfite modification and use the same as a control group that contains non-methylated promoter sequence.

Use qMSP primers and probes to perform methylation specific quantitative PCR analysis on 1 μg sample genomic DNA that has been modified by bisulfite and control DNA. The qMSP primers and probes specifically recognize methylated gene sequence. The sequences of the qMSP primers and probes for each target gene are shown in Table 1. The total volume of methylation specific quantitative PCR product is 20 μl comprising 1 μl modified template DNA, 250 nM of each primer, 225 nM of fluorescence probe and 2× FastStart Universal Probe Master (Rox) (Roche). The mixed reactants are placed in ABI 7900HT Fast Real-Time PCR System. The initial denature is performed at 95° C. for 10 minutes followed by denature at 95° C. for 15 seconds, annealing at 60° C. and synthesis for 1 minute as a cycle. The denature, annealing and synthesis steps are repeated for 45 cycles. Methylation quantitative data analysis is performed using SDS 2.3 software, setting the threshold=0.128 and the baseline between 3 to 15. Based on the methylation Index (Meth-Index) formula: $[100,00 \times 2]^{\wedge}[(COL2A\ of\ Ct)-(Gene\ of\ Ct)]$, subject the internal control gene COL2A and the quantitative data of methylation specific genes to calculation for the degree of methylation of target genes in the samples.

TABLE 1

Sequences of MSP primers used in Methylation Specific PCR

| Gene Name | Species of primers/probes | Sequences of primers/probes | |
|---|---|---|---|
| ADRA1D | M Positive strand(F') | 5' ggttaggtagtttcgttttcggatagtc 3' | SEQ ID No: 10 |
|  | Negative strand(R') | 5' aaacacaaaacgaacgaccgaca 3' | SEQ ID No: 11 |
| AJAP1 | M Positive strand(F') | 5' tttggtagagtttttcgattcggtagc 3' | SEQ ID No: 12 |
|  | Negative strand(R') | 5' accgaaactccgcgccgataa 3' | SEQ ID No: 13 |
| HS3ST2 | M Positive strand(F') | 5' gtaagagtttgggagcgttcgagtc 3' | SEQ ID No: 14 |
|  | Negative strand(R') | 5' caaaaaatcccgaaaacaacgac 3' | SEQ ID No: 15 |
| MAGI2 | M Positive strand(F') | 5' cgtagagttcgagatgtggtattaggc 3' | SEQ ID No: 16 |
|  | Negative strand(R') | 5' aaactcctatacgaaaaaaacgcgcta 3' | SEQ ID No: 17 |
| POU4F2 | M Positive strand(F') | 5' tactcccctcaaacttaaatcctttc 3' | SEQ ID No: 18 |
|  | Negative strand(R') | 5' gcgggacgttgcgaag 3' | SEQ ID No: 19 |
| POU4F3 | M Positive strand(F') | 5' agcgcgggcgttgagtagc 3' | SEQ ID No: 20 |
|  | Negative strand(R') | 5' cgcgctcctaacaaaataacaacgaa 3' | SEQ ID No: 21 |
| PTGDR | M Positive strand(F') | 5' ttgtttcgcgtttttaatgttagc 3' | SEQ ID No: 22 |
|  | Negative strand(R') | 5' aaaaaaactccgaaaacgacgaaat 3' | SEQ ID No: 23 |
| SOX17* | M Positive strand(F') | 5' ggagattcgcgtagttttcg 3' | SEQ ID No: 24 |
|  | Negative strand(R') | 5' aacccgaccatcaccgcg 3' | SEQ ID No: 25 |
| SYT9 | M Positive strand(F') | 5' tggggtcgtcgttatttattttgc 3' | SEQ ID No: 26 |
|  | Negative strand(R') | 5' ccgcccgatccctccgtc 3' | SEQ ID No: 27 |

Primer species M represents the MSP primer that can specifically recognize methylated gene sequences The purpose of using pyrosequencing to analyze the fragment of target gene is to accurately quantify the percentage of degree of methylation on CpG sites of the target genes. Before performing pyrosequencing, the software PyroMark Assay Design 2.0 (QIAGEN) should be used to design the primers for biotin marker. Use PCR amplification to cover the gene fragment of target gene CpG sites followed by pyrosequencing to detect the percentage of methylation on CpG sites of the target genes. First of all, add the Pap smear cell or tissue sample DNA that has been modified by bisulfite to the primer pairs containing biotin label and the PCR reaction solution of PyroMark PCR kit (QIAGEN). After PCR amplification of target fragment, check whether the PCR amplified fragment is correct with 2.0% agar gel. Perform purification and denature of the DNA sample using PyroMark Q24 Vacuum Workstation (QIAGEN). After addition of sequencing primers, perform pyrosequencing and methylation analysis using PyroMark Q24 System (QIAGEN).

Example 2: Screening of Methylated Target Genes

Screen 14,475 genes using Infinium HumanMethylation27K methylation chips.

(1) Select those having higher methylation rate score (β value >0.4 and <0.4), combine Gene Expression database (GE07803), and analyze gene enrichment (The Database for Annotation, Visualization and Integrated Discovery, DAVID). 92 genes are selected;

(2) Cancer cell lines are treated with 5-AZc and TSA. Analyze the 92 genes using QRT-PCR to confirm that gene expression is influenced by methylation. 61 genes are left;

(3) Mix the samples to be detected and use MSP to analyze DNA methylation of the 61 genes. 26 genes are left;

(4) Analyze DNA methylation in cancer samples for the 26 genes by MSP. 21 genes are left;

(5) Analyze DNA methylation in cancer tissues for the 21 genes by MSP. 16 genes are left;

(6) Analyze DNA methylation in cancer samples for the 16 genes by Q-MSP. 14 genes are left.

Confirm the methylation status of genes by pyrosequencing. The selected final nine target genes may be highly methylated in cancer cells. The genes are: ADRA1D (SEQ ID No: 1), AJAP1 (SEQ ID No: 2), HS3ST2 (SEQ ID No: 3), MAGI2 (SEQ ID No:4), POU4F2 (SEQ ID No:5), POU4F3 (SEQ ID No:6), PTGDR (SEQ ID No:7), SOX17 (SEQ ID No:8) and SYT9 (SEQ ID No: 9). The detailed information is shown in Table 3. From Table 3, it can be known that while HS3ST2 is known to be associated with colon cancer and breast cancer and POU4F2 and SOX17 are known to be associated with breast cancer and liver cancer, there are few researches that demonstrate the association between these genes and cervical cancer or other cancer.

TABLE 3

The detailed information of methylated genes selected with Infinium HumanMethylation27K methylation chip in cervical cancer or other cancers

| Gene name | UniGene number | Location in chromosome | Gene full name | SEQ ID No |
|---|---|---|---|---|
| ADRA1D | NM_000678 | 20p13 | alpha-1D-, receptor | SEQ ID No: 1 |
| AJAP1 | NM_018836 | 1p36.32 | adherens junctions associated protein 1 | SEQ ID No: 2 |
| HS3ST2 | NM_006043 | 16p12 | heparan sulfate (glucosamine) 3-O-sulfotransferase 2 | SEQ ID No: 3 |
| MAGI2 | NM_012301 | 7q21 | membrane associated guanylate kinase, WW and PDZ domain containing 2 | SEQ ID No: 4 |
| POU4F2 | NM_004575 | 4q31.2 | POU class 4 homeobox 2 | SEQ ID No: 5 |
| POU4F3 | NM_002700 | 5q32 | POU class 4 homeobox 3 | SEQ ID No: 6 |
| PTGDR | NM_000953 | 14q22.1 | prostaglandin D2 receptor | SEQ ID No: 7 |
| SOX17 | NM_022454 | 8q11.23 | SRY (sex determining region Y)-box 17 | SEQ ID No: 8 |
| SYT9 | NM_175733 | 11p15.4 | synaptotagmin IX | SEQ ID No: 9 |

Example 3: Methylation Analysis of Target Genes in Cervical Cancer Samples

Use methylation specific PCR (MSP) to analyze the methylation status of the nine target genes in cervical squamous cell cancer samples. The results show the degree of methylation of ADRA1D, AJAP1, HS3ST2, MAGI2, POU4F2, POU4F3, PTGDR, SOX17 and SYT9 in normal cervical samples (SCC N) (the medians are 0.34, 0.18, 0.19, 2.58, 7.62, 0.77, 0.16, 0.17 and 0.31, respectively); and the degree of methylation of ADRA1D, AJAP1, HS3ST2, MAGI2, POU4F2, POU4F3, PTGDR, SOX17 and SYT9 in cervical cancer samples (SCC T) (the medians are 911.37, 1558.97, 1088.65, 713.92, 535.01, 1552.71, 305.84, 248.29 and 551.84, respectively). After Mann-Whitney test, the two groups of data reach P<0.0001 among each group. The difference is statistically significant. The above are as shown in FIG. 1(A), FIG. 2(A), FIG. 3(A), FIG. 4(A), FIG. 5(A), FIG. 6(A), FIG. 7(A), FIG. 8(A), and FIG. 9(A).

Example 4: Methylation Analysis of Target Genes in Ovarian Tumor Samples

Use methylation specific PCR (MSP) to analyze the methylation status of the seven target genes in ovarian tumor samples. The results show the degree of methylation of ADRA1D, AJAP1, HS3ST2, MAGI2, POU4F2, POU4F3 and PTGDR in benign ovarian tumor samples (ovary N) (the medians are 4.25, 5.19, 0.00, 10.91, 2.06, 3.60 and 1.57, respectively); and the degree of methylation of ADRA1D, AJAP1, HS3ST2, MAGI2, POU4F2, POU4F3 and PTGDR in malignant ovarian tumor samples (ovary T) (the medians are 13.62, 10.76, 114.38, 33.08, 4.28, 21.97 and 28.40, respectively). After Mann-Whitney test, the two groups of data reach P<0.05 among each group. The difference is statistically significant. The above are as shown in FIG. 1(B), FIG. 2(B), FIG. 3(B), FIG. 4(B), FIG. 5(B), FIG. 6(B), and FIG. 7(B).

Example 5: Methylation Analysis of Target Genes in Liver Cancer Samples

Use methylation specific PCR (MSP) to analyze the methylation status of the five target genes in liver cancer samples. The results show the degree of methylation of ADRA1D, POU4F2, PTGDR, SOX17 and SYT9 in normal liver tissue samples (HCC N) (the medians are 35.29, 6.25, 49.30, 20.15 and 19.70, respectively); and the degree of methylation of ADRA1D, POU4F2, PTGDR, SOX17 and SYT9 in liver cancer samples (HCC T) (the medians are 202.10, 53.73, 275.76, 111.25 and 154.65, respectively). After Mann-Whitney test, the two groups of data reach P<0.0001 among each group. The difference is statistically significant. The above are as shown in FIG. 1(C), FIG. 5(C), FIG. 7(C), FIG. 8(B), and FIG. 9(B).

Example 6: Methylation Analysis of Target Genes in Colon Cancer Samples

Use methylation specific PCR (MSP) to analyze the methylation status of the eight target genes in colon cancer samples. The results show the degree of methylation of ADRA1D, AJAP1, HS3ST2, MAGI2, POU4F2, POU4F3, SOX17 and SYT9 in normal colon tissue samples (colon N) (the medians are 59.21, 228.97, 292.95, 123.44, 591.64, 249.72, 80.12 and 52.63, respectively); and the degree of methylation of ADRA1D, AJAP1, HS3ST2, MAGI2, POU4F2, POU4F3, SOX17 and SYT9 in colon cancer samples (colon T) (the medians are 83.47, 2312.91, 2301.12, 799.41, 1615.48, 1058.53, 751.06 and 601.65, respectively). After Mann-Whitney test, the two groups of data reach P<0.05 among each group. The difference is statistically significant. The above are as shown in FIG. 1(D), FIG. 2(C), FIG. 3(C), FIG. 4(C), FIG. 5(D), FIG. 6(C), FIG. 8(C), and FIG. 9(C).

Example 7: Methylation Analysis of Target Genes in Breast Cancer Samples

Use methylation specific PCR (MSP) to analyze the methylation status of the nine target genes in cervical squamous cell cancer samples. The results show the degree of methylation of ADRA1D, AJAP1, HS3ST2, MAGI2, POU4F2, POU4F3, PTGDR, SOX17 and SYT9 in normal breast tissue samples (breast Ca N) (the medians are 11.78, 22.28, 112.81, 24.55, 30.23, 31.29, 43.64, 12.02 and 5.53, respectively); and the degree of methylation of ADRA1D, AJAP1, HS3ST2, MAGI2, POU4F2, POU4F3, PTGDR, SOX17 and SYT9 in breast cancer samples (breast Ca T) (the medians are 57.19, 260.96, 281.64, 193.70, 77.06, 310.34, 341.97, 77.05 and 25.24, respectively). After Mann-Whitney test, the two groups of data reach P<0.01 among each group. The difference is statistically significant. The above are as shown in FIG. 1(E), FIG. 2(D), FIG. 3(D), FIG. 4(D), FIG. 5(E), FIG. 6(D), FIG. 7(D), FIG. 8(D), and FIG. 9(D).

Example 8: Methylation Analysis of Target Genes in Oral Cancer Samples

Use methylation specific PCR (MSP) to analyze the methylation status of the seven target genes in oral cancer samples. The results show the degree of methylation of ADRA1D, AJAP1, HS3ST2, MAGI2, POU4F2, PTGDR and SYT9 in normal oral tissue samples (oral Ca N) (the medians are 10.25, 0.0065, 115.98, 0.00, 30.23, 10.47 and 0.00, respectively); and the degree of methylation of ADRA1D, AJAP1, HS3ST2, MAGI2, POU4F2, PTGDR and SYT9 in oral cancer samples (oral Ca T) (the medians are 26.44, 0.0107, 381.49, 54.59, 77.06, 32.78 and 10.85, respectively). After Mann-Whitney test, the two groups of data reach $P<0.05$ among each group. The difference is statistically significant. The above are as shown in FIG. 1(F), FIG. 2(E), FIG. 3(E), FIG. 4(E), FIG. 5(F), FIG. 7(E), and FIG. 9(E).

Example 9: Methylation Analysis of Target Genes in Endometrial Cancer Samples Use methylation specific PCR (MSP) to analyze the methylation status of the seven target genes in endometrial cancer samples. The results show the degree of methylation of AJAP1, HS3ST2, MAGI2, POU4F2, POU4F3, PTGDR and SYT9 in normal endometrial tissue samples (Em N) (the medians are 0.00, 0.00, 0.00, 16.42, 0.31, 0.00 and 0.63, respectively); and the degree of methylation of AJAP1, HS3ST2, MAGI2, POU4F2, POU4F3, PTGDR and SYT9 in endometrial cancer samples (Em T) (the medians are 535.78, 1456.23, 504.15, 248.83, 89.86, 148.19 and 0.43, respectively). After Mann-Whitney test, the two groups of data reach $P<0.05$ among each group. The difference is statistically significant. The above are as shown in FIG. 2(F), FIG. 3(F), FIG. 4(F), FIG. 5(G), FIG. 6(E), FIG. 7(F), and FIG. 9(F).

Example 10: Methylation Analysis of Target Genes in Sarcoma Samples

Figure 4:
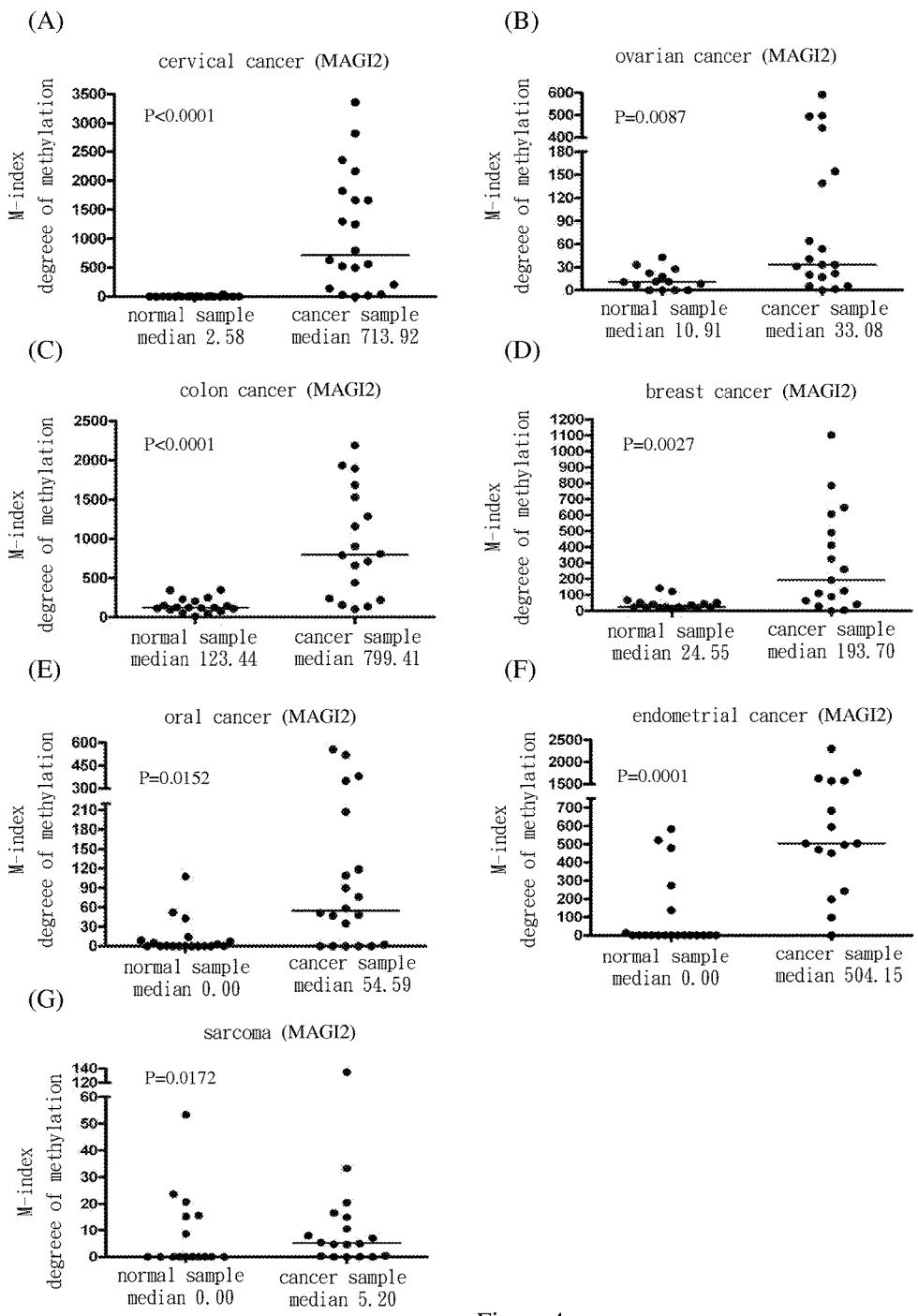
FIG. 4 shows the result of degree of methylation of the target gene MAGI2 used in the method of screening cancer of the present invention by bisulfite sequencing (BS) in various normal and cancerous tissue samples: (A) uterine cervix, (B) ovarian tumor, (C) colon, (D) breast, (E) oral tissue, (F) endometrial tissue, and (G) sarcoma.
Figure 5:
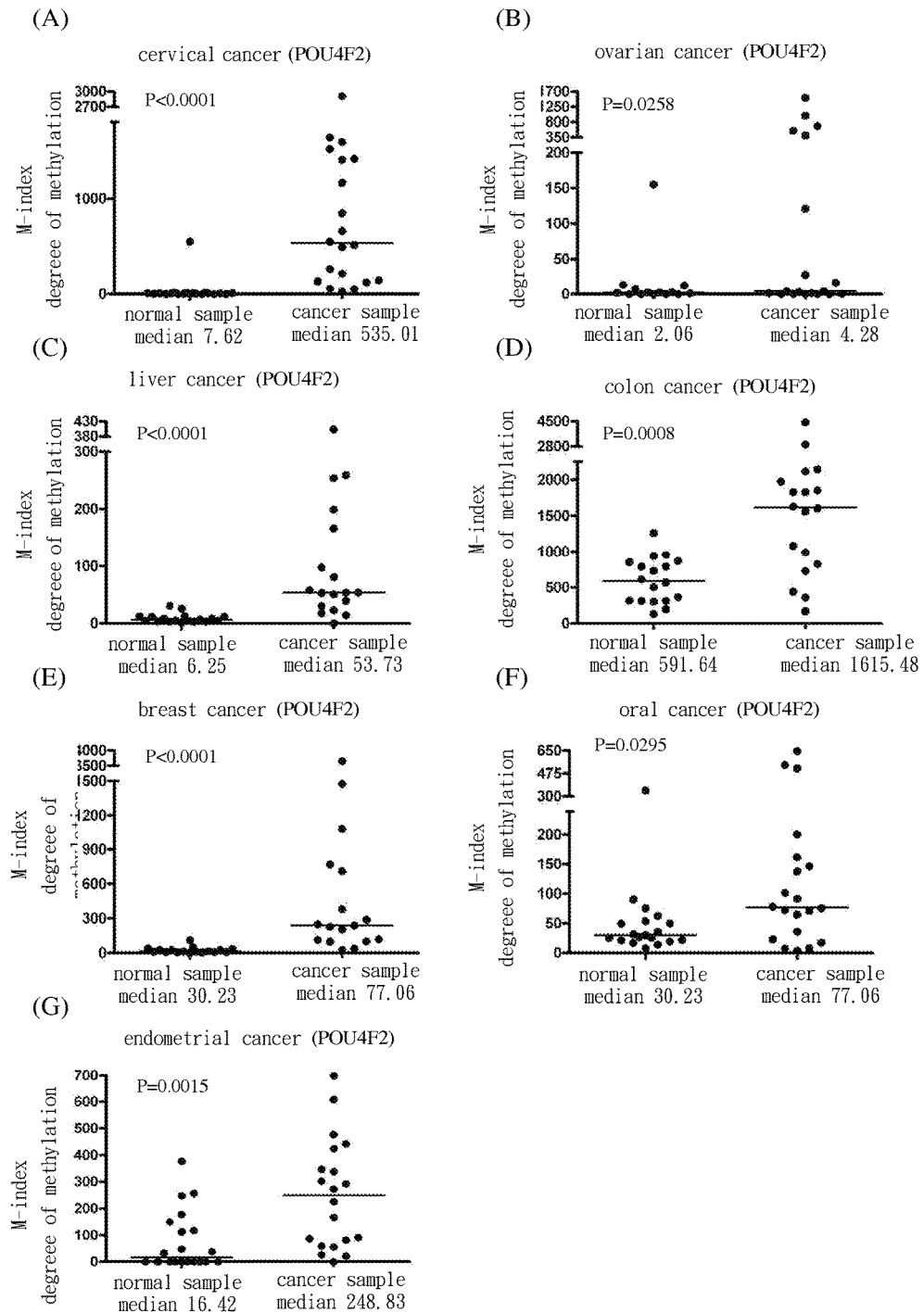
FIG. 5 shows the result of degree of methylation of the target gene POU4F2 used in the method of screening cancer of the present invention by bisulfite sequencing (BS) in various normal and cancerous tissue samples: (A) uterine cervix, (B) ovarian tumor, (C) liver, (D) colon, (E) breast, (F) oral tissue, and (G) endometrial tissue.
Figure 6:
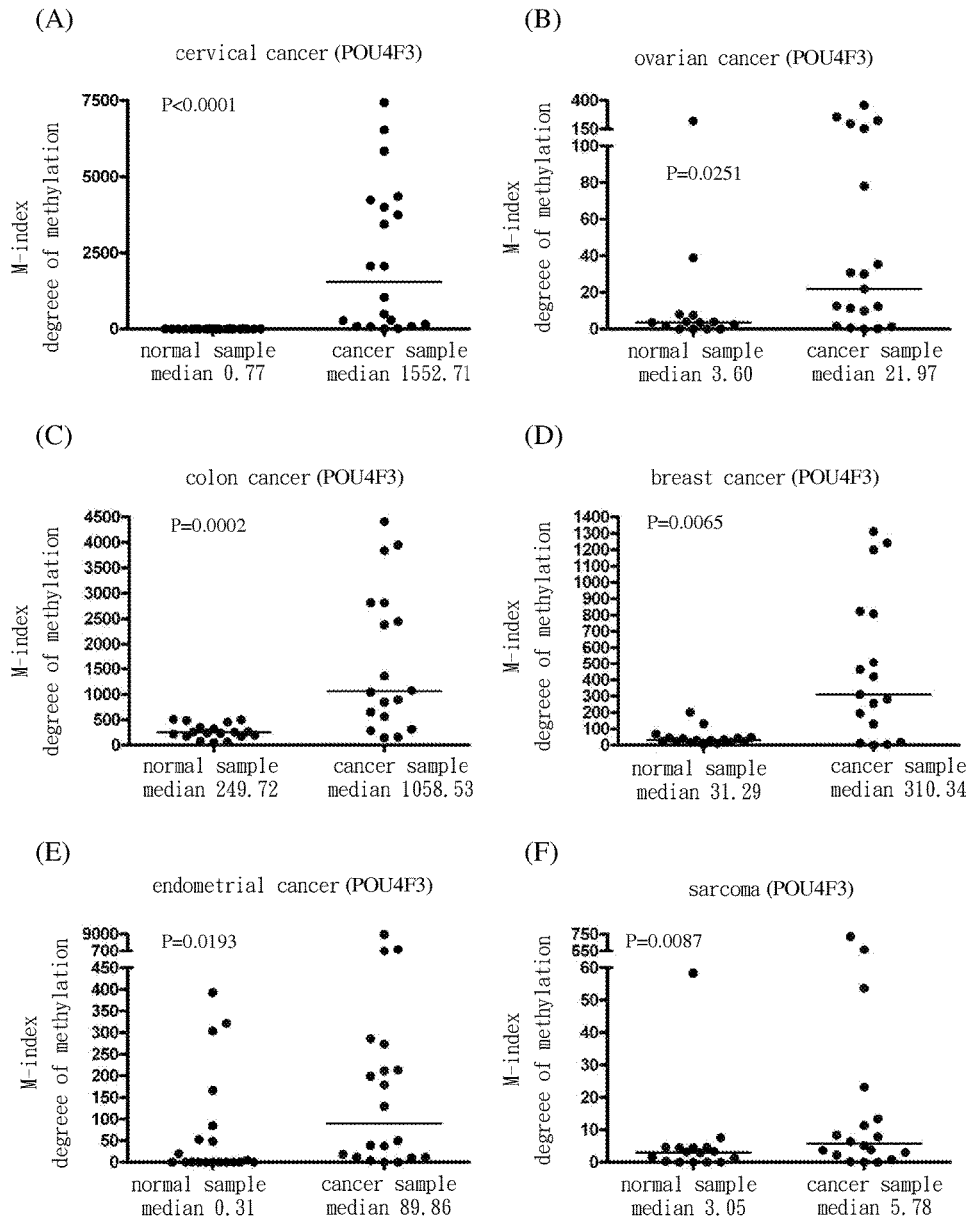
FIG. 6 shows the result of degree of methylation of the target gene POU4F3 used in the method of screening cancer of the present invention by bisulfite sequencing (BS) in various normal and cancerous tissue samples: (A) uterine cervix, (B) ovarian tumor, (C) colon, (D) breast, (E) endometrial tissue, and (F) sarcoma.
Figure 7:
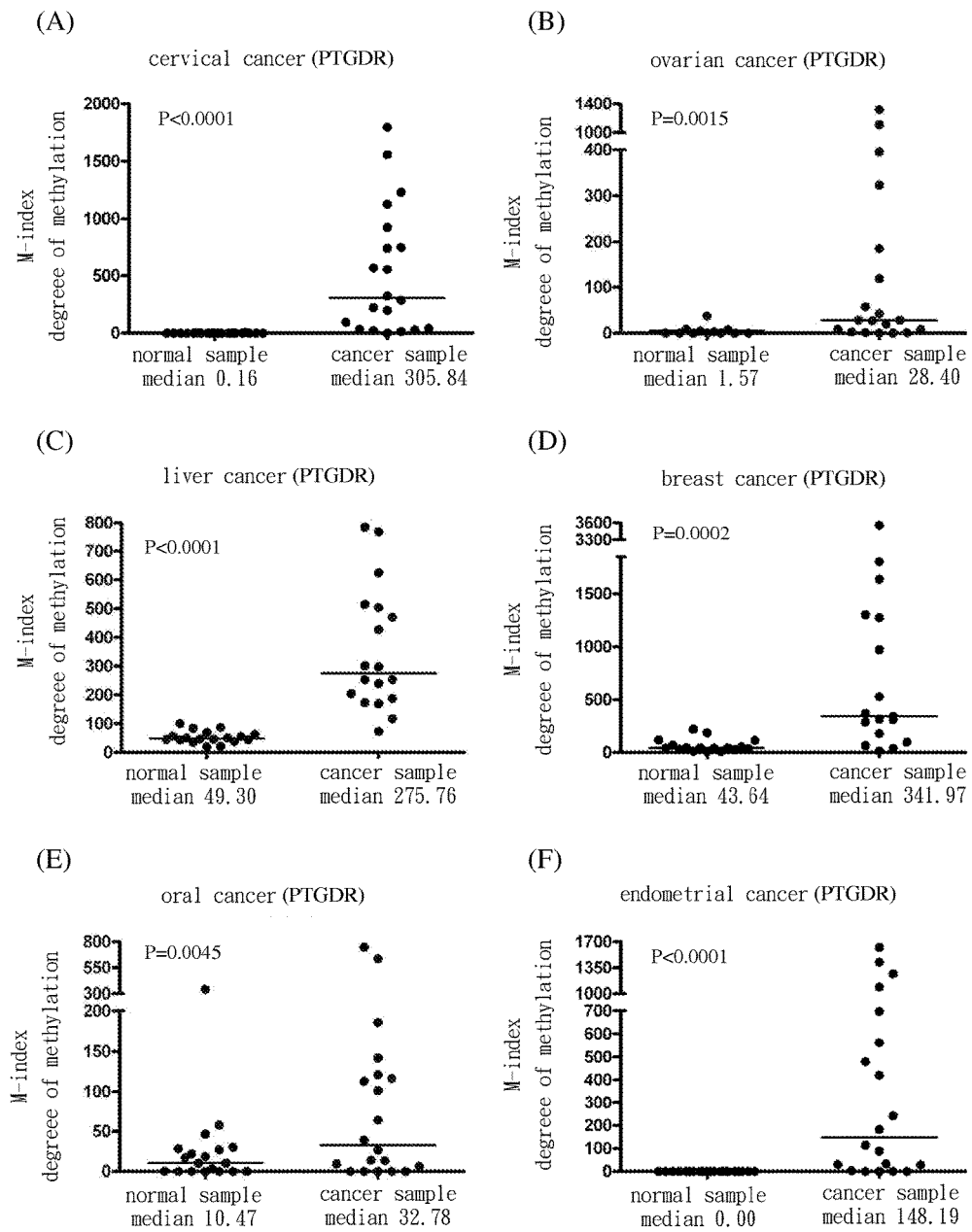
FIG. 7 shows the result of degree of methylation of the target gene PTGDR used in the method of screening cancer of the present invention by bisulfite sequencing (BS) in various normal and cancerous tissue samples: (A) uterine cervix, (B) ovarian tumor, (C) liver, (D) breast, (E) oral tissue, and (F) endometrial tissue.
Figure 8:
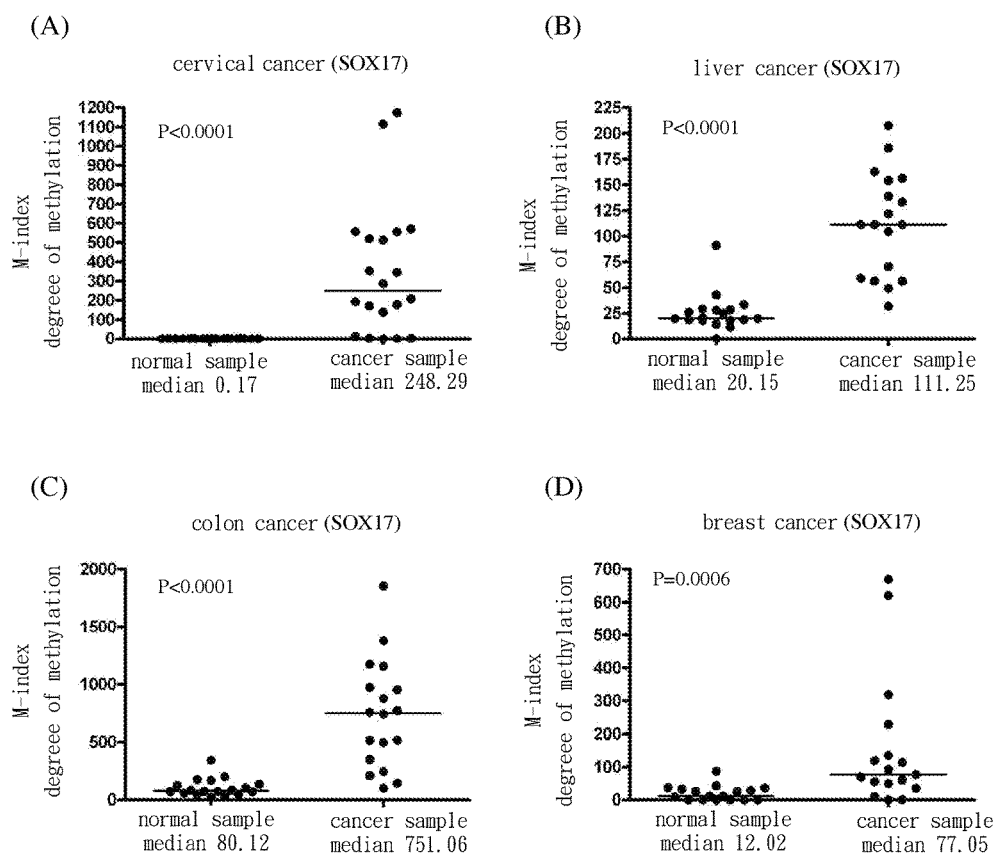
FIG. 8 shows the result of degree of methylation of the target gene PTGDR used in the method of screening cancer of the present invention by bisulfite sequencing (BS) in various normal and cancerous tissue samples: (A) uterine cervix, (B) liver, (C) colon, and (D) breast.
Figure 9:
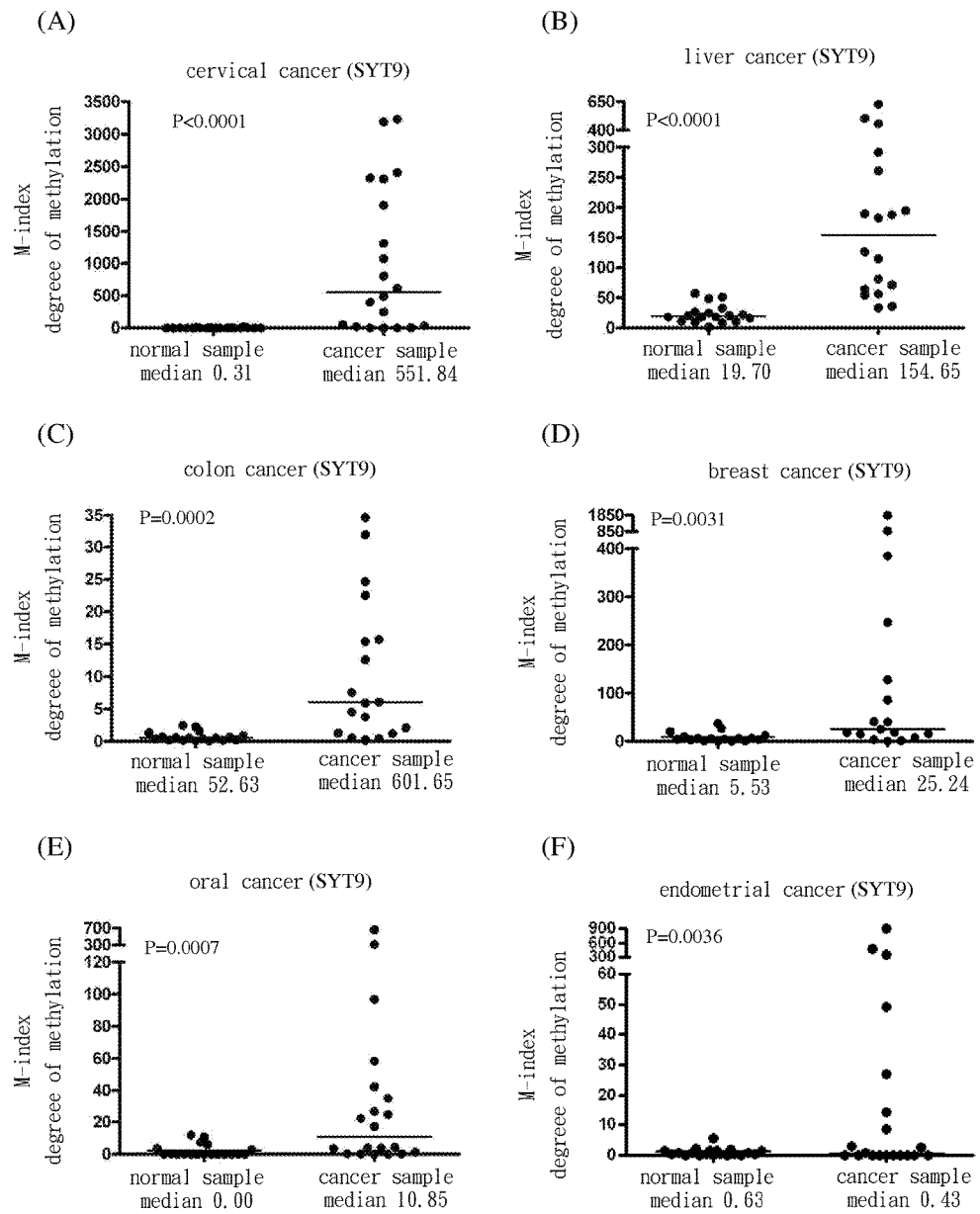
FIG. 9 shows the result of degree of methylation of the target gene SYT9 used in the method of screening cancer of the present invention by bisulfite sequencing (BS) in various normal and cancerous tissue samples: (A) uterine cervix, (B) liver, (C) colon, (D) breast, (E) oral tissue, and (F) endometrial tissue.

Use methylation specific PCR (MSP) to analyze the methylation status of the two target genes in sarcoma samples. The results show the degree of methylation of MAGI2 and POU4F3 in benign sarcoma samples (sar N) (the medians are 0.00 and 0.31, respectively); and the degree of methylation of MAGI2 and POU4F3 in malignant sarcoma samples (sar T) (the medians are 5.20 and 89.86, respectively). After Mann-Whitney test, the two groups of data reach $P<0.05$ among each group. The difference is statistically significant. The above are as shown in FIG. 4(G) and FIG. 6(F).

The above detailed descriptions are specific illustrations to the embodiments of the present invention. However, the examples are not used to limit the patent scope of the present invention. The equivalent practice or alteration that do not deviate from the present invention such as alteration in the way to determine the degree of methylation of each target gene in the specimen to be detected and equivalent examples, should be covered in the patent scope.

What is claimed is:

1. A method for screening cancer, which detects the methylation status of target gene in the cells of a specimen, and methylation status is an indicator of the presence or absence of cancer, wherein the method comprises the following steps:
   (a) providing the specimen in which the methylation status will be detected;
   (b) detecting the methylation status of a CpG sequence the target gene POU4F3 in genomic DNA of the specimen, wherein the methylation status is detected by a primer pair having at least 80% sequence identity or complementarity to each primer in the primer pair SEQ ID NO: 20 and 21, or at least 10 contiguous nucleotides identical to each primer in the primer pair having the nucleotide sequences as set forth in SEQ ID NO: 20-21; and
   (c) determining whether cancer or precancerous lesions are indicated in the specimen according to the methylation status of the target gene.

2. The method for screening cancer according to claim 1, wherein the specimen to be detected is Pap smear, ascites, blood, urine, feces, phlegm, oral mucosal cells, gastric fluid, bile, cervical epithelial cells, or an in vitro sample of cancer tissues after surgery.

3. The method for screening cancer according to claim 1, wherein the method of detecting methylation is methylation specific polymerase chain reaction or quantitative methylation specific polymerase chain reaction.

4. A method for screening cervical cancer, which detects the methylation status of target gene in the cells of a specimen, and methylation status is an indicator of the presence or absence of cancer, wherein the method comprises the following steps:
   (a) providing the specimen in which the methylation status will be detected;
   (b) detecting the methylation status of a CpG sequence the target gene POU4F3 in genomic DNA of the specimen, wherein the methylation status is detected by a primer pair having at least 80% sequence identity or complementarity to each primer in the primer pair SEQ ID NO: 20 and 21, or at least 10 contiguous nucleotides identical to each primer in the primer pair having the nucleotide sequences as set forth in SEQ ID NO: 20-21; and
   (c) determining whether cervical cancer or precancerous lesions are indicated in the specimen according to the methylation status of the target gene.

5. The method for screening cervical cancer according to claim 4, wherein the specimen to be detected is Pap smear, blood, cervical epithelial cells, or an in vitro sample of cancer tissues after surgery.

6. The method for screening cervical cancer according to claim 4, wherein the specimen to be detected is abnormal Pap smear.

7. The method for screening cervical cancer according to claim 4, wherein the specimen to be detected is cervical cell specimen which is positive in human papilloma virus testing.

8. The method for screening cervical cancer according to claim 4, wherein the method of detecting methylation is methylation specific polymerase chain reaction or quantitative methylation specific polymerase chain reaction.

9. A method for screening ovarian cancer, which detects the methylation status of target gene in the cells of a specimen, and methylation status is an indicator of the presence or absence of cancer, wherein the method comprises the following steps:
   (a) providing the specimen in which the methylation status will be detected;
   (b) detecting the methylation status of a CpG sequence the target gene POU4F3 in genomic DNA of the specimen, wherein the methylation status is detected by a primer pair having at least 80% sequence identity or complementarity to each primer in the primer pair SEQ ID NO: 20 and 21, or at least 10 contiguous nucleotides identical to each primer in the primer pair having the nucleotide sequences as set forth in SEQ ID NO: 20-21; and
   (c) determining whether ovarian cancer or precancerous lesions are indicated in the specimen according to the methylation status of the target gene.

10. The method for screening ovarian cancer according to claim 9, wherein the specimen to be detected is ovarian cancer tissue, ascites, blood, or an in vitro sample of cancer tissues after surgery.

11. The method for screening ovarian cancer according to claim 9, wherein the method of detecting methylation is methylation specific polymerase chain reaction or quantitative methylation specific polymerase chain reaction.

12. A method for screening colon cancer, which detects the methylation status of target gene in the cells of a specimen, and methylation status is an indicator of the presence or absence of cancer, wherein the method comprises the following steps:
   (a) providing the specimen in which the methylation status will be detected;
   (b) detecting the methylation status of a CpG sequence the target gene POU4F3 in genomic DNA of the specimen, wherein the methylation status is detected by a primer pair having at least 80% sequence identity or complementarity to each primer in the primer pair SEQ ID NO: 20 and 21, or at least 10 contiguous nucleotides identical to each primer in the primer pair having the nucleotide sequences as set forth in SEQ ID NO: 20-21; and
   (c) determining whether colon cancer or precancerous lesions are indicated in the specimen according to the methylation status of the target gene.

13. The method for screening colon cancer according to claim 12, wherein the specimen to be detected is colon tissue, ascites, blood, feces, or an in vitro sample of cancer tissues after surgery.

14. The method for screening colon cancer according to claim 12, wherein the method of detecting methylation is methylation specific polymerase chain reaction or quantitative methylation specific polymerase chain reaction.

15. A method for screening breast cancer, which detects the methylation status of target gene in the cells of a specimen, and methylation status is an indicator of the presence or absence of cancer, wherein the method comprises the following steps:
   (a) providing the specimen in which the methylation status will be detected;
   (b) detecting the methylation status of a CpG sequence the target gene POU4F3 in genomic DNA of the specimen, wherein the methylation status is detected by a primer pair having at least 80% sequence identity or complementarity to each primer in the primer pair SEQ ID NO: 20 and 21, or at least 10 contiguous nucleotides identical to each primer in the primer pair having the nucleotide sequences as set forth in SEQ ID NO: 20-21; and (c) determining whether breast cancer or precancerous lesions are indicated in the specimen according to the methylation status of the target gene.

16. The method for screening breast cancer according to claim 15, wherein the specimen to be detected is blood, milk, secretions of the breast, cyst, puncture and biopsy specimen, or an in vitro sample of cancer tissues after surgery.

17. The method for screening breast cancer according to claim 15, wherein the method of detecting methylation is methylation specific polymerase chain reaction or quantitative methylation specific polymerase chain reaction.

18. A method for screening endometrial cancer, which detects the methylation status of target gene in the cells of a specimen, and methylation status is an indicator of the presence or absence of cancer, wherein the method comprises the following steps:

(a) providing the specimen in which the methylation status will be detected;

(b) detecting the methylation status of a CpG sequence the target gene POU4F3 in genomic DNA of the specimen, wherein the methylation status is detected by a primer pair having at least 80% sequence identity or complementarity to each primer in the primer pair SEQ ID NO: 20 and 21, or at least 10 contiguous nucleotides identical to each primer in the primer pair having the nucleotide sequences as set forth in SEQ ID NO: 20-21; and (c) determining whether endometrial cancer or precancerous lesions are indicated in the specimen according to the methylation status of the target gene.

19. The method for screening endometrial cancer according to claim 18, wherein the specimen to be detected is blood, vaginal-flushed substances, menses, tissues from dilatation and curettage of uterine, or an in vitro sample of cancer tissues after surgery.

20. The method for screening endometrial cancer according to claim 18, wherein the method of detecting methylation is methylation specific polymerase chain reaction or quantitative methylation specific polymerase chain reaction.

21. A method for screening sarcoma, which detects the methylation status of target gene in the cells of a specimen, and methylation status is an indicator of the presence or absence of sarcoma, wherein the method comprises the following steps:

(a) providing the specimen in which the methylation status will be detected;

(b) detecting the methylation status of a CpG sequence the target gene POU4F3 in genomic DNA of the specimen, wherein the methylation status is detected by a primer pair having at least 80% sequence identity or complementarity to each primer in the primer pair SEQ ID NO: 20 and 21, or at least 10 contiguous nucleotides identical to each primer in the primer pair having the nucleotide sequences as set forth in SEQ ID NO: 20-21; and (c) determining whether sarcoma is indicated in the specimen according to the methylation status of the target gene.

22. The method for screening sarcoma according to claim 21, the specimen to be detected is blood, or an in vitro sample of cancer tissues after surgery.

23. The method for screening sarcoma according to claim 21, wherein the method of detecting methylation is methylation specific polymerase chain reaction or quantitative methylation specific polymerase chain reaction.

* * * * *

SEQUENCE LISTING

```
<160> NUMBER OF SEQ ID NOS: 27

<210> SEQ ID NO 1
<211> LENGTH: 3500
<212> TYPE: DNA
<213> ORGANISM: Homo sapiens

<400> SEQUENCE: 1
ctccttgcct cccctttcag ttcccactgt ccctccctc tcagaaagga agcccaaacc      60
caagatttta cttttggtca gctgctagct aatccctaga agccacgttg ctttcgtttc     120
aactcactat agtaagtttc caaaaccaa aataaaagaa gatttaatgg ggaaggcctt      180
ggaagagctg tttccaagct atgattataa aagccttatc ttcctggact gggcaatggg     240
gaggagggag gccacccatc tctaaacatt tctgcagttt tttacttttt ctccaaagca     300
gcttctcatc tagaactcag acatcctgcc cctgtgtcaa ccataaccag tgaacactag     360
ggctatgggt tctccgtccc ctcccagaca cttctgcaaa caggccttca tctccctggt     420
agggctcaag ccctcctcat tctgcaacta tgagacggca ttaccctcct tacagttagt     480
gtatccagca tggtgcctgc cacgtgccag cagccggtat ttttatgttg gctaactgta     540
tgatttcctt gtgcctctcc ctacccagtc ctgctattgc tcaagaagct tctcacaccc     600
tctcccacat ctgcacccgg ggtccatacc agccccacac ctcctcgcct tccatcctcc     660
ctgttaaaag cctgccctga agaagcccta ctccgctgac atgcccaggc actgctctgg     720
ggccctcact catatttact cagttaaccc tcaggccagg aggtagacat cacttcttat      780
tctcatttga cagttgagga actgaggcac aaagaggttc cgctgttaat atggggcgga      840
```

```
gcctggattc agatgcggag ccagactgtc tcacacccgc ccgcttaac catcctgcca    900
agtgcccttt cccaccctct ggcacttaaa ccctccctct taaaaaggcc agaacaagaa    960
caaggcccct tatttagggt agctatagaa aggtttattc ccgcatctga tacagggaaa   1020
agtaacagtg ggaaagttgg cgtatgtaga ccagcgtgtc ttgggcaggg tccgagggct   1080
gtagccacag cctgctgctc ctgagcccat cgtacccagc ctctgcccag cacaggcttc   1140
cgacccttcc tgggctctct tcacgccatc gcactggaca gaggcgtctg aaaccctgcc   1200
ctggccagtg gcgtgagaaa aaggaggtgc ggcagatcca tgcgggcagt cccaggaggc   1260
aacccgcagc ggcactgcgc cgtccggtcc gcagtccgca gatcccaggc gcttgctgct   1320
ctctggcggc caaagccggg atcccgaaga cccgggactc acgccttcaa cgcaccgcgc   1380
gcccaagggc accagcgagt gaccgagaga ctcgggggag agggcgggag gaagagggac   1440
gccgctgagg gccaaggggg aggggtccg ggagaggagc gggaaggaac gcaaagggca    1500
ccgctaggga gagcgcggg cttgggcacc tgcggagagg cgtgggtggc tgctgcggga    1560
cccgagcgcg cgccagcgcc gcagccccc ggaccccgac acaatcgctt gtcctgagcg    1620
aagggtccct tctaccctgg agtgtggcgc ccgtctctcg gcccgggtcg ccccctcctc   1680
cttcctggcg ctgccccctcc tcggtcccgc ccccgcgcc gagttgggag cgccgcagtg    1740
gccgctgcct gcaccgcccg gccccggagc cgccgctttg cccgcttgcc gggcacgctc   1800
agagcgccgc gcgcgtagcg ggccccggct cttcggtgct actccacggc cggcctcggg   1860
gagcccggcc gccgcccggg ccaggcagct ccgctctcgg acagccgcgc tccgcgtcac   1920
aggaacttgg gcaggacccc gacgggaccc gtgcgcggag ctgcatctgg agccccgcgg   1980
ctatgccctg tgctcccctc cctgccggcc gctcgttctg tgccccgcc cggccaccga    2040
cggccgcgcg ttgagatgac tttccgcgat ctcctgagcg tcagtttcga gggacccccgc  2100
ccggacagca gcgcagggg ctccagcgcg ggcggcggcg ggcagcgc gggcggcgcg      2160
gccccctcgg agggcccggc ggtgggcggc gtgccggggg gcgcgggcgg cggcggcggc   2220
gtggtgggcg caggcagcgg cgaggacaac cggagctccg cggggagcc ggggagcgcg    2280
ggcgcgggcg gcgacgtgaa tggcacggcg gccgtcgggg gactggtggt gagcgcgcag   2340
ggcgtgggcg tgggcgtctt cctggcagcc ttcatcctta tggccgtggc aggtaacctg   2400
cttgtcatcc tctcagtggc ctgcaaccgc cacctgcaga ccgtcaccaa ctatttcatc   2460
gtgaacctgg ccgtggccga cctgctgctg agcgccaccg tactgcccct ctcggccacc   2520
atggaggttc tgggcttctg ggcctttggc gcgccttct gcgacgtatg ggccgccgtg    2580
gacgtgctgt gctgcacggc ctccatcctc agcctctgca ccatctccgt ggaccggtac   2640
gtgggcgtgc gccactcact caagtaccca gccatcatga ccgagcgcaa gcggccgcc    2700
atcctggccc tgctctgggt cgtagccctg tggtgtccg tagggccct gctgggctgg    2760
aaggagcccg tgcccctga cgagcgcttc tgccgtatca ccgaggaggc gggctacgct   2820
gtcttctcct ccgtgtgctc cttctacctg cccatggcgg tcatcgtggt catgtactgc   2880
cgcgtgtacg tggtcgcgcg cagcaccacg cgcagcctcg aggcgggcgt caagcgcgag   2940
cgaggcaagg cctccgaggt ggtgctgcgc atccactgtc gcggcgcggc cacgggcgcc   3000
gacggggcgc acggcatgcg cagcgccaag ggccacacct tccgcagctc gctctccgtg   3060
cgcctgctca gttctcccg tgagaagaaa gcggccaaga ctctggccat cgtcgtgggt   3120
gtcttcgtgc tctgctggtt ccctttcttc tttgtcctgc cgctcggtga gtgaccccte   3180
```

| | |
|---|---|
| tcccaccggc ccctcctgtt ctccctgagc ctatggcggt gccctcctgg cacccagact | 3240 |
| tgggcgaccc ccacctgaac ctagaaggtt gacttagcaa gtcctgagtc tcctaagagg | 3300 |
| caggtgtgca tgcaccattt tgtggagtgc aaggaacgg ttcttcatcc tcgccaggtt | 3360 |
| cgtttcacag gcttctaact tttctgtcct tcccttcttc ttttccaagc cttgggctta | 3420 |
| tgctgctggc ccctctaaaa ataaaacgtc tgtgaaaatc tgggcgggca tctgcccata | 3480 |
| tgtggtcggc agtgtatgtg | 3500 |

```
<210> SEQ ID NO 2
<211> LENGTH: 3500
<212> TYPE: DNA
<213> ORGANISM: Homo sapiens

<400> SEQUENCE: 2
```

| | |
|---|---|
| acagatgagg agaccgaggg tcggagaggc cacacaactc ggccaggacc ccgagttagc | 60 |
| aagcgctggc ccctggtcca gccacggcaa ggctggccct cctgccacca cacttccctg | 120 |
| cctctggccc tctgccggga gtcttggtgg ggaagtcact gtcttcatcc tcctgcccgg | 180 |
| gcagagtcca atcctgtgcc tggctcctca agaccgttgg caaagatcct ggaggcctgg | 240 |
| gggtgaaagg gctgcttggg ggacttaagc cccaagctat ggttcgcctg ggagactgag | 300 |
| ccccaagcca tggtcctcct ggctctgccc ttccacccc tcactggctg ccctccccag | 360 |
| ggaggcctca cctgtgaagt gcttcccgcc cctctcaccc ccacggctc tcacatggcc | 420 |
| tggggcgatt ccagagctgg cctgggtcaa gcacctgcac agagcacaga gcgaaggctc | 480 |
| ggcatggtat atccccgcc ccttgcacct ttccccagtg aagggtggca ccagtgtcct | 540 |
| ttccaaggcc cggattctgc actgccctca gcctgtggag gattaaaagc agggttttgc | 600 |
| cgtggtttct caaggcgtca gcgggtctgc agaggattcc gccccatgtc acttctctca | 660 |
| gtgaaaggtc cccgcccagc gtctgtcctc ctttaagtgc cccccatttg ttttttgttg | 720 |
| ttgtttttgt ttgtttttg caaatacaga ctaaccaggt aggcacagag gagtcctggc | 780 |
| atgggaaggg agcagtgaaa cgccggtgga gagtccggga ggcccagatt ccctggaact | 840 |
| ttccagtgac tcctccggag caagggcctg ccaggcagc agctgcgctg ggcgatgagg | 900 |
| gaccgttggg taattggggg cataggaccg ggcttcgctg ggttcggggc agaagcgccg | 960 |
| aagctccgac ccggaacgcg gtgacttcat caacgcagaa gcccgcgcag ccgagcagag | 1020 |
| gagtccctcg taggcgaccc tcggacagac gctcctgcgc ggcccgcgtg gctcagctcc | 1080 |
| gccccaggaa acttttcgcg cagccccgc tccatgcgcc cccacccagt ccttcttcgg | 1140 |
| ggccgccccc tccccaaagt agctctccgg gtccactggg cgccccgta accgggtcgg | 1200 |
| aacctcgaac ggcttcgcgt gccatccggt taccctggca acaccatccg gcggcgcccg | 1260 |
| gcggtccaat cctagcctgc ggcctctctc gagcctttcg caaggtgggg accgggacgc | 1320 |
| gaccggggat ggggaagggg gctgcaggag ccccgcctg cgctgtcgcc cctgctgggc | 1380 |
| acagcgcccc ccaccacccg cggcgacccc ggccccgca aggtggggcg gcgagcagga | 1440 |
| gccggggcca ggccagggc tcgagctccc gttcgagggg cgggaaggc gggtgacgtg | 1500 |
| agccgggccg ggcgggcgga gttgggaccg gctccgggag gcggggcga gcgcgcggag | 1560 |
| aggcagacgc gaggagggag gcggctgagc agcgcgggcg gctctgcggc gggcgcggtg | 1620 |
| ggcgcggggcg gcggggcccc gggatcccg cgcgcctcct ccgcgcgcg ccgccgccgc | 1680 |
| gcgtccccac gccccgcgct ccacggcgcc ctcgccccgc gcgcctctcg tgcccgcctc | 1740 |
| ctgccagtct ccgggccgcg gccgtctgca gagcgagcgc tcagacggag ccccgggca | 1800 |

```
acttgagtgg cgccgatcgg cggcggagcc tctggcagag cccccgaccc ggcagcgcg    1860
gaggggactc gcgtccgtcc gcgtcgcgtc accccaaacc ctaagcagcg ccgcccatc    1920
ggcgcggagc tccggctgga ggcaagagcc gcgcgccggg agacacgcac cgtgagcggc    1980
agcgccgccg gcctccctcc tcgccgcccc ggagggcgaa ccgcggctc cccagcccctt    2040
tgctgcgccg cgacagcgcc ggaacacgcc ccgcctcgct gccgccttcg ctgtgccgcc    2100
ggcggagggg gccgcgagcc ccgcgccccg gccgaggat gtgcgccccc gcgggccgcc    2160
cagcctgagc catgcgcccc aacggcggcg gcgcgccggc cggcatggag ccccgcgcgg    2220
ccgcgctctg actcgctgtg cgccccgcgg ccggcgggcg gcgggaggcg gcggaccgag    2280
agccggagac cggcgccgcg ggacggaagc gagcgggcgc gggcgccgcg cagatggcct    2340
gggcgagcca ggtctgaggc cccgctcccc gaaacgtgac catgtggatt caacagctt    2400
taggactcag gtgagcgacc cggccggcgc cgggtgcgtg tgggcgcgtg ggtgccaggc    2460
tgggcggaag cggcgctttc ctctatgttg caaatcaagg gacccctctt cgcttcccgc    2520
aagcgggcaa cggggtgcac cggtagccgg aaaggggcgc ccgcccggag cctggagcag    2580
caccgcggcc ctggcgggga gcggccgggt ctccagggtt ccgcgcgtcc ggggtcgggg    2640
cagcggcgcc cgccccagca acccgggaag tggggccggc caggcgcgcc cgcagctcta    2700
ggagccagca gcgcagtgtc ctggccggct gccccggcgc gcctcctccc cggggcccgg    2760
ggcgaggcgc cggccgctgg gcgcggcggg cgcggggggcc ggggctgccg gggaaagcta    2820
aagctccggg ctcccagcga gagcttcgca ggcggagttg gaggaaacca cagccaaaca    2880
gccactccgc tccccttct cctttctcgg ggccccgggg ctgagcaggg gcctcccagg    2940
ctcccagctg ccgacccagc tgtttgcggg tgacctccgg gcccgacggg cgctcacagc    3000
tggcgggcag ctgggcggg agagctgggg ttcttgggga gctccggcgg ccaccccgct    3060
gtaaacacac acgcacatac gcccgccggc gcgcccgggg cttgtctgtg tctgggactc    3120
cagggccaga tggaagaggg ggttcgagcc tagagcccgt ggtgggggtg tccagaaaga    3180
cccttctcgg caaactttgc cagcccgccg gggttctcgg gcttctctgg cttctgcctg    3240
gggtggccca gggcccacca gagcacagct gtcgtttttg ctgggcaggc tgcctctgag    3300
ccctcgccct cctgccgggg cattcaccga gctcgtgcat ttgggtcccg ggttggaacc    3360
gcgagcgggg aggacagagg tggaggcgga gagcagcgtg cggttctcga gtttgtccac    3420
tgggatgcac tgcgctcccg cgttggggac gaaaaggcca gtagttgtta gcccgctgct    3480
tgagccgccc ccactcaggg                                              3500
```

<210> SEQ ID NO 3
<211> LENGTH: 3500
<212> TYPE: DNA
<213> ORGANISM: Homo sapiens

<400> SEQUENCE: 3

```
aatcttctta tcactgcctg tagattagaa attacaataa tacctatctc caaagataaa     60
tgaggtagtg catgtcaagt gattagcgca taactcccat aaaacaagca ctcaataaat    120
gctagctact attagaatta agacagcaaa gtgatgccag gtaatggta acaacttcat    180
aggttgtgaa tatttaatca gttaacccat gccaggtgct tgatacaaag ttggcagcta    240
ttattattat ctgccgtaga attggtttaa ggtttctagg gatgggacta gtttggggac    300
aaaatatttt ctggtttggg ctaagatcca cagaacctaa tgatcagttt acagcctgag    360
```

-continued

```
gaaggaagtc agttatacco tgatcagggt gggggtcatg gtggtcatct agacattcta      420
tggctgggtg gtggtggagg gcactcacct tgtgaacact cggacatggt gaattggcat      480
tggcattgct gttgaaggac aactcagccg tgttcttagc catggccatt taggcctgtt     540
ctgatgcagg gttctgatcc aaggtaccag tgtggtccct cagggaagta ctggggatcg     600
tcacttatgc ctgttctgga catggtcacc gagaactgtc ctgtaggcat tcacttagga     660
atcattcgaa gtggaattgc tcctggatac gttctccttg tactctgttt cctcctccta     720
gtgtctctgt gtgaagaagc cctcctcact cagccctcgg cgaccctctg tacccctgga     780
cagctccccg gggagcagtc taccgctagg cggcggctgc taagagagga accctcctga     840
cgcggagtct gccgctccgg ggctcgctct ccggcaggcc cggggagagg tggggtgaca     900
atgggttggg gtgcgcgcgt gcctcatagg tgcgagacag agcgagccgc cggggtgtga     960
gtcagcgcgc tgggggctaa aagctgggt gaatagtcac ggaatctcac tcacgctcgg     1020
ctcctccacc catcccgtct acagcgcgtg tcccagtcca gggcgtgcgt gcgctcggtg    1080
tccgattccg ggctgtgtgt gtccatttgg cgagatgtcg agagcggggg gagtgtcctt    1140
gtcggtgtat ctgggcccag gttaggggac ttctcctccc caccccgcg tgggtgtggg     1200 ggtgtgtccg ggctagggcg cgtgtgcttc tgtgcctgtg cgtgcgtgtg cgggtcaggg    1260
tggtgggacc gcgcatcagg gcagggtgcc tgcgtctgcg tctgggtctg tctggtctgc   1320
atgtcggcgc gatctcgacc tggattcgtg tccctggatg tcgagaggcc agcgtggtgg    1380
gggtgtccag cctcccggag gagtactatg ccttgacacc ttcgtttcac cgccccaaag   1440
ctggcctggg gctccgtagg gagtggcctg catgggagg gccgcgtgc tgtgtttctg     1500 ggagggtaa gagagtgggg gcgcagggg cgggccaggt ccctgggcgc ggcgcgggct     1560 cggggggaccc gcgcggctga cgtcaggcca ctccttaaat agagccggca gcgcgctccg   1620
ctcggcattt cccgaagagc cagatcgcgg ccggcgccag cgccaccgtc cggtccaccc   1680
gccagcccgc acagccgcgc cgccgccgag cgtttcgtga gcggcgctcc gaggatcagg   1740
aatgggcctt cgggcgctgg gcgcgctccg aaccggcgc acgtaagagc ctgggagcgc    1800
ccgagccgcc cggctgcccg gagccccatc gcctaggacc gggagatgct ggaaatgcaa    1860
ccgcctgttc cccgaggagc cgctgccccc gggaccccct ggcactgtgc gcaccctggt   1920
cagcagcccc cggagaagac ggcgccccca acgcccgacc cgcgtggccg tggcagcgcc    1980
acgcgagccc tctaggcgac cgcagggcca cagcagctca gccgccggtg cccctcgga    2040 aaccatgacc cccggcgcgg gcccatggag ccatggccta tagggtcctg ggccgcgcgg    2100
ggccacctca gccgcggagg gcgcgcaggc tgctcttcgc cttcacgctc tcgctctcct    2160
gcacttacct gtgttacagc ttcctgtgct gctgcgacga cctgggtcgg agccgcctcc    2220
tcggcgcgcc tcgctgcctc cgcggcccca gcgcgggcgg ccagaaactt ctccagaagt    2280
cccgcccctg tgatccctcc gggccgacgc ccagcgagcc cagcgctccc agcgcgcccg    2340
ccgccgccgt gcccgcccct cgcctctccg gttccaacca ctccggctca cccaagctgg   2400
gtaccaagcg gttgccccaa gccctcattg tgggcgtgaa aagggggggc acccgggccg   2460
tgctggagtt tatccgagta cacccggacg tgcgggcctt gggcacggaa ccccacttct    2520
ttgacaggaa ctacggccgc gggctggatt ggtacaggta aggaccagga gctccgctcc   2580
gtgcgccggg tctctgatcg cttccattgg gagagccatc cgtctcttgt gttttctctt   2640
tcttttaacc caactcattg tatgggttca ggctgacaca cagggccatg gggggctata    2700
gcagaattta cccagaactt cccagtgata atctagacgg gcagtttctg gaactgcaaa    2760
```

| | |
|---|---|
| gggcgttccc tcgtcactgg agtcgttgga aaaggattat ctccagtcaa acctaagtgc | 2820 |
| cagctaaagg gctaactccc tctgtgacca gcccttaggg tgcccaagga agggacaggc | 2880 |
| gaggacctgt gctgcctgaa cacggcacca tcctaaccct ctgtaggtct ttgctggtac | 2940 |
| ccagcccctg aaggaccctg agaaagataa ggcagttcag agacccctlg cagcaaggct | 3000 |
| ctgtttggga aaggtcccca gagttcaggc caaatgacag tgcatcgcca gaggtctcca | 3060 |
| gtaagaaaga tgccttaggg agtctcaatc tcaaacccag gtatttgctg ctgtactggg | 3120 |
| gctgagaccc ccagtagctc tggccctggt aggtggtctt tgagtagtgg aaagagccct | 3180 |
| ggattcgagt cttgggtctg tcacttaagc ttgagcaagt tcttaaaact ctatcagcct | 3240 |
| ctattttctc atccatccca atgggcagga aaacagccct tgccctgtat accttccaag | 3300 |
| gcttttctga agtgccttaa aggtgtaaaa aaggcacttc actttaagtg atgcttctaa | 3360 |
| accagcagcc aaaatgtgga atttgaaggt gggccctgcg ggtgaaggct agcaagggtg | 3420 |
| ctaggggcag ccagtcatgc atagactgtc tatgcttccc atgcatgcca gggaggagaa | 3480 |
| ttatccccac tgggggagtc | 3500 |

<210> SEQ ID NO 4
<211> LENGTH: 3500
<212> TYPE: DNA
<213> ORGANISM: Homo sapiens

<400> SEQUENCE: 4

| | |
|---|---|
| cactgaataa gcttcaacta gtgcagccaa cttacggagg atctgttttc tcaagtgaaa | 60 |
| aaaagacaca aggttaaaca aatcatcttt ttttaagatc tcttccagtt ctgactacat | 120 |
| ttgatccccc tcatccccaa gtagtaagtt atacctaaga gggaaagagg agggaattat | 180 |
| catttcgaac tcctactcac ctgtgccagg agagcactgc tgtgactgat ttccctgatt | 240 |
| tcatcctcac cacagtccta acagattagt attgttaaag tccatttaac aactaagaaa | 300 |
| gctgaggctc aggaaggtca agcagtttac tcaagatcat attctcagta agccgcagag | 360 |
| tctggattga aacctggtct ttctgtttgg gtcgactcaa cattttttaac cgtattgttt | 420 |
| gcctcctaca tcgccttcat ctcagacatt aagaatccta cctattcaat gcttttcatc | 480 |
| ctccgcttta aagagataag tgggtgcaca acttttttttt tgcctgaaac atatcatcta | 540 |
| aaagttaagc aaatgaaatt catttaccag ttacaggaat cttttcttta aatcactgtt | 600 |
| aatgtctcac aggaaattag ctcttcagtg gaaatcagca gcctccctgc atccttttgc | 660 |
| ccctgtcctc ccctctcttg gatgcaaacc tggcgaaaag aagggaacac tgcttggggt | 720 |
| cagcgagctg agttccagct ccgaatgtac cattttcacc ctcgggagtc ttctcccctt | 780 |
| tctctgtgag caaaggagtg ttgggccaga ccgtcttaag gattcttccc caggtacaag | 840 |
| ccggactctg gcggctttcc tgggcaaggg agtgtctccg ccttgtctct gccgcaggtc | 900 |
| cctggttaaa ttgtcaattt ctctgcggag gctgctcact gcatccgctc cctccacccc | 960 |
| tagccctgta gaccccttct cttttcccta cttgggaaaa gtgaagcccc ttatccttgg | 1020 |
| atagcctttc accagacaac cgcagccgtc cgctaaattc ccctactggc gggacgcgcg | 1080 |
| ggcgggggcc tgccccgggg aatgcgaggc tgcttccctt ctgcgtaatc agggtacgca | 1140 |
| gcctccagtt ctctaacttt ctccttctct aagagggaat ttcgagaact ttaagacaaa | 1200 |
| taagtgacta tatagatgaa gacatgaaac ctctctacac agtgaactcc ccacgctac | 1260 |
| aaggctccca gggatcccag gccttctccc gcaatgcccc gccgggtccc ccgccccaac | 1320 |

-continued

```
tccttctcac ggcaggatcc cgcgccagga cgctcgcaga gcccgagatg tggcaccagg      1380
cgcgccacaa gtccaggtcc cgctatttct gctccatcgg agcccaggtc ggagggagtc      1440
agcgcgtcct cctcgcacag gagcctggcg cgcggctcgg tcgcacagag gctgaagaaa      1500
ggtccgcact gggctcgagg cccttcctgc cggcctcccc acgccgggcc taggctcccc      1560
tccttcccgg ctcccgcctc ctcccgtagg ctgccaggcg gacccagcct gcctctctct      1620
ctgccttcac taccgggtca agctgcggag ggagggaggg aggcagcggc gaagccctcc      1680
gtggctcccc accggcgcg cgcgccctc ctccctgcc tctcccgtc tgccagtaca          1740 gtagaactag tacacacaca cacacacaca cacgcaca cgcaccctgc cactgcagct        1800
gccatggata tcagctaaca acacacaccc aggcgcgcg gcgcgttccc actcgcacca      1860
cgcaggagtg gccccggca tcctaccct ccttccccac ccccaccaca cccgctcacc        1920
agctcggcta ctgctcgctc cggctgccgc cgccgccgcc gccgacgcca ccaccactgc      1980
ttcctctgct gcggggccac agccttgagt gtcattcaag gacagcaca acctcatcca       2040 agctctccta cctctgccca gccgtccctc tcatcctccc cattcctcgt ccacactcca      2100
tccaaagaag agggaaagca ccgaatagag gggggcgaag gcaaagtctg ctgttcttcc      2160
ccctgggccc ccttgctcct ccatcctcat tctctcacca ccagccccc taaccccaag      2220 gagcccagga actgaggcga ctcgccccac tgccatgtcc aaaagcttga aaaagaaaag     2280
ccactggact agcaaagtcc atgagagtgt cattggcagg aacccggagg ccagctgggg     2340 cttttgaactg aagggggcg ccgagaatgg acagttcccc tacctggggg aggtgaagcc      2400
cggcaaggtg gcctatgaga gcggcagcaa attggtgtcg gaggagctgc tgctggaggt     2460
gaacgagacc cccgtggcgg ggctcaccat cagggacgtg ctggccgtga tcaaacactg     2520
caaggacccc ctccggctca agtgtgtcaa gcaaggtgag agcagcggct tgctcagtgt     2580
tttgccgggc ggtgggaccg ctcggggcgc agggcaatga agggtggcc gcgcatgttg      2640 aaggggtgt gttgcgcgat gatggggtgg gggccagaga gcacccgcag tgcaagtgag      2700
tttcgccggg gattcgactt gggggctaaa gggaggggag gggcaggttg tggtgtggcg     2760
tgcaactttg tttgctcagt tagacccctcc cctttggaag gtgctcggcc tggtctgacc    2820
tcctcagagc tgctggggca aattgaatgt gcgtcagtgg catcacccga agcggatgaa     2880
gagcttttgg ggaagggagg aaggaagaaa agaaagaaag aatggaggga agggagggaa     2940
agaaggaagg agcaacttca gggtgcagcg gcatcaccag cgggtctggg aagagaaggt     3000
ggtggggtga gcggagaact gcgtccagcg tttctggggc tgggctgggg gcgcctgggt     3060
ccccagctgt cccttaggga tccgtgagcc accgctggcg aagaaaagaa gggacaaatt     3120
gctttgggcg ctttgacggg tcttctgtaa cttttccccct tcttcactcc gtgtcccct     3180 cccccgctca cggtcgtgtc atgtgggcat cgcgcgtcac gtgcgtactg actaacccct    3240
gcgctcaccc ctagccagcc cggggagga ggctccggaa gaaggcgcgg tgctaggagc     3300
gcagtctagt gctgggcggg ggtcggagga gatgaatggt tgtcggagga gatgaatggt    3360
tgtccgcatg gactttactc aggggttgcc ctcattgagt ggaagtcctc tgtggttggg    3420
ctctcctctg gctccgattt gggggcgtg ttttggggga ggagctggat gaaaccctgg     3480
ccggttccag cccaggctcc                                                3500
```

<210> SEQ ID NO 5
<211> LENGTH: 3500
<212> TYPE: DNA
<213> ORGANISM: Homo sapiens

<400> SEQUENCE: 5

```
cattcacgtg aacactcccc tttccctacc ccatgtccag gtttcgctga gctcacaccc      60
ggcaacactg ctgctaggag ttcccttcgg ctactattta ttattttcct ccacacaggg     120
gaagagaaag ggaagcccga gaggatccag ggaaagcaga aggggggttaa ggaccatgga    180
cagagcccgt cgcgcgctcg ttgctgccgc cttccccagc actctggcgg ctcctgagga    240
cagcggtccc atcttgaaac cgctattccg cccggctgag gtcaggggtg acaggcggt     300
cccctactct ccaccgccgc ttccgggagc tgaccacccg agggttcccc ttttccactc    360
tccttcccac tctgttttg tcccagcgcg cgccagcgcc tctcaggcct gccgcctgct      420
ctcgcacctg ctcgccttcc ccaggcgccc agtgcctgca cctgctcccg gtcaaccccc    480
gtccggattg ggccaccgc gggttcctgc gtcggggtcc cggggccttc tcaccctcgc     540
ctgcaccctg ctccttccgc tctctaggga ggtgacagca gccccaaca ccgcgggaag     600
tatagagaaa atgggatcca gaaggagagg aagtagtgtg tgtgtgtgtg tgtgtgtgtg    660
tgtgtgtgtg tgacagagag agagagatag atagaaagag attatctcct tttgcaactg    720
gaaccaagag tgtgtgtcca tctctaggaa aagtggtctg cactgggact gggacagaag    780
tgggagtgaa gtgtcagcta aaaataggct ccgcaccgag aggctgtgga aatgaagata    840
agtgaggttt gtgccagccc ccgagggtgt gtgtgtgtgt gtctgtgttg tggggtgtat    900
tcagcagcat atgcgctgtg taatttctga ccttccctct ccctgtcagt tgcccttct     960
tcctttgatt gtggctaatg aagaataata aatccagggg cagggtttgc cagtggatcc   1020
ttccaagact caactcgaac tgtactggat acagggagga ggaggaagag aaaaggggggg  1080
caagaggagc gtgtgtgtgt gcctgtgtgt atgtgtgtgt gtgttgtggg aggggtgggg   1140
acagcgggga gggggaggag tcgcatgcgc acagacgacc cgagcctgct ccgcggctgt   1200
ccaatccgct gagagctgcg agaaatcgag tgagagaaag ccctgcagcc cctccgaccc   1260
catgtctctt tggcaccagg caccccgccgg gccgtggggg gctcgtagcc gaacgccgac  1320
ctccgctcgt attgggctgg gagttcagag ccgcgcgcag aacccgggtt ggccgcaacg   1380
tctgtgttct cagcggtggc cgggaacctg ggatcagggt cacctgagct gacggggtgg   1440
gggcgggccg agtgggggttg gaagcctgga acttagtggt aagcaggagg cgtaggaggt   1500
ggcagccagg taagaggcac tcttacctac ccaacgctgg cttgggccgc aactttattt   1560
gggagtttct ttttccggtg agacagagac ccggcagaag aagcgggagg ggctggaggc   1620
tggtccttag gtaggcactg cccggcgact ggagcgcgga cctggccatt tgggtggggt   1680
tgagtggggg cgcgattgtg agtagcagcc gcgggacgct gcgaaggggc ggcggcaaca   1740
gagcacgggc gggggcagaa aagaggcggc ggagggcgcg gtggggagc gcgaggcgag    1800
tgctgagaga gcagaaagga ctcaagcctg aggggagtag agaggaagaa gggcaacgc    1860
gagaaaccga acaggagccg gcgtttcctg gcaaggggagg gcggaggcgc gcgggagaga   1920
gggagagagg gagggcgggg ggcgcggggg taggcgcggg gagaggggag tataactcgc    1980
cggccgcgag gagcggggc agtttcgggt gccgaggtct gcagctagcg gcaagcggag    2040
tcaggcatcc gttcagactg acagcagagg cggcgaagga gcgcgtagcc gagatcaggc   2100
gtacagagtc cggaggcggc ggcgggtgag ctcaacttcg cacagccctt cccagctcca   2160
gccccggctg gccggcact tctcggaggg tcccggcagc cggaccagt gagtgcctct     2220
acggaccagc gccccggcgg gcgggaagat gatgatgatg tccctgaaca gcaagcaggc   2280
```

-continued

```
gtttagcatg ccgcacggcg gcagcctgca cgtggagccc aagtactcgg cactgcacag      2340
cacctcgccg ggctcctcgg ctcccatcgc gccctcggcc agctccccca gcagctcgag      2400
caacgctggt ggtggcggcg gcggcggcgg cggcggcggc ggcggcggag gccgaagcag      2460
cagctccagc agcagtggca gcagcggcgg cggggggctcg gaggctatgc ggagagcctg      2520
tcttccaacc ccaccggtgc gtatttctgc ataatcaccg cttaaaggca cattttgaca      2580 gccccctttta tctgcttgat gttttttttca tgtctgcaca gcaaatcacc ccacacctcc      2640
aaccaatttt ccctctctc tctcttaagt attcagcagg tcttgccttt catattaatt      2700
tttatgacct gggatgttgc ctgtgcgcgt gttgtgttgt gtttcgttgt gtctacaggc      2760
tcactttcct cctcctcctg cactctcggc ttctttctgt ggcttccctc tttttctctt      2820
cacctctgtt ttcaggatta ttattattat tattttaacg atctgggaat gttgtaggcg      2880
cggcgacggt gtcgagccct gggccggggc ttccggagag agggcgtaca attccctgct      2940
gagcgtaatg tgtgccttct acttacaatt gcagagcaat atattcggcg ggctggatga      3000
gagtctgctg gcccgcgccg aggctctggc agccgtggac atcgtctccc agagcaagag      3060
ccaccaccac catccacccc accacagccc cttcaaaccg gacgccacct accacactat      3120
gaataccatc ccgtgcacgt cggccgcctc ttcttcatcg gtgcccatct cgcacccttc      3180
cgcgttggcg ggcacgcacc accaccacca ccatcaccac caccaccacc accaaccgca      3240
ccaggcgctg gagggcgagc tgctggagca cctgagtccc gggctggccc tgggcgctat      3300
ggcgggcccc gacggcgctg tggtgtccac gccggctcac gcgccgcaca tggccaccat      3360
gaaccccatg caccaagcag cgctcagcat ggcccacgcg cacgggctgc cgtcgcacat      3420
gggctgcatg agcgacgtgg acgccgaccc gcgggacctg gaggcattcg ccgagcgctt      3480
caagcagcga cgcatcaagc                                                 3500
```

<210> SEQ ID NO 6
<211> LENGTH: 3332
<212> TYPE: DNA
<213> ORGANISM: Homo sapiens

<400> SEQUENCE: 6

```
ccgcagtaca gagaagttga gaatatctcg tggtctcagc cagcaagagg cagaggcgca       60
ttttgaatct gaggccaggg cctgagcgct atggcaccag gttgtgaggg agtttactga      120
gcaccaattt cgtggctcaa tgcttttctt cttaccctaa ctctgaacgt cttcaccaga      180
atccaaggag gcagacagta gtgcaattcc atttaagagc cgccgaaacc gaggctcaga      240
gggctttagc gaaagggttg cgcttggctc taggcacctg ggctgagtct ttttcccacc      300
atcgcagggc gggaaccagc ggaggggggct ggctcggatg gggagaaaag caactggagg      360
gcgccgaggg gaagagggag cccggatctg tcagggcgtc ctcttggact aagggatgtt      420
cccctaaacc acaccacccc acctcgttca gattctggga aacccggcac gcacataccc      480
tgcacaataa caggcagggt gaggtctcta agccccgaag atcgctctct cagcggaggc      540
agtggccctg acgaggggggt acagctgcac gcgcggggtt tctctccgaa ccggagtgca      600
gcgtagtcga ggtccaggat tccccatcca ttattcacga tgtttactag agcggggcaa      660
gggagaggaa agaagaggga agtagagaga aaagaggct aggggaggtg gaggcgggca       720
gtgctaacct cgagagccct caagttccga aactttgaga aggaagacca agaggctaag      780
gcgcctggga agcagcaggc cgtcagtaaa tatttgtaag atggatggat aactgggtga      840
gtgagtgaat gggctaatca ttagccctc tgatcctttgt tttcctcatc tgtaaaacgg      900
```

-continued

```
gataacatca cctactccat acggtgggta tgagaatccc atgggcaaac tctaaattgt    960
ctagcacata ttaggaactc ttaaacggta gctgttgtca cgaggaatgg gcttgcaagc   1020
tctggctgcc cagcagaaat gcactgaagg actcccaggc ctggagggcc atcctgaaca   1080
gtcgctattc taaaaaaaat actccacaag cttccttaga cgggagggtt ggaggaagag   1140
tgggccaagt tacatccctc aaatgaaaga agaaaggca agcgtgggga ggaagccacc    1200
ccggactgag aaggcagtta ctgcccctac ctctaccccg agcgcggtt gagggaggtg    1260
gggcagggt cacctgggcc tcgttctggc agcccctcac cctctccagg gcccgtctgg    1320
gcgcttggag gcgcctcctc gctgcgccgc gggaccggac tctggtggac agcttgggcg   1380
tgaggccagg agcgccctgg aaatgggcag tttggcggca gccgggccga cggagtgtgt   1440
gtgtgtgtgt gtgtgtgtgt gtgtgtgtgt gtgtgtggtg gagaggggaa gttggagtag   1500
ggtcaacttc ctgccccagc tcagcccagg gctacccttt tatccaggca gttcgagctg   1560
ggacaggacg gagaggttgg gacttttggg gtggcatggg ggaagggaag tccacgaaga   1620
agaaagaatc ggaaaggtct ggcgggttgg agccagcggg gcggggcgga ctgggagagg   1680
ccaggccagg cccgggtata aaggctgtgg aggggggcgc cgccgcgggc gcagaaaggc   1740
gcgccgctag ctgctgtctc tcctcacctc ccgggccgcc cctgcgagtc cccggcgcgt   1800
gagcacgcct gcgcgcgccc gggcccttcc tggcaggctg cttgtaagat gagtgaagaa   1860
gcaggtgggg gagaggggag gcagcgagcg agagggcgag gggagcgcgg gcgctgagca   1920
gcgctcactt ggagagcggc aagcaagcta gacaagcctg attccatgtc acccgctgcc   1980
accctgccag gagcgcgaag atgatggcca tgaactccaa gcagcctttc ggcatgcacc   2040
cggtgctgca agaacccaaa ttctccagtc tgcactctgg ctccgaggcc atgcgccgag   2100
tctgtctccc agccccgcag gtacgtagtg gagcataatt accgctctaa ggcacatttt   2160
ttgacaggca ctagcttcat gttttttca tgtcgcccag aacaatcgcc gctgtctgaa   2220
cccctctcct tgtctccccc gcgttctctc ccggcgcgct ctctctctca ttcatgtctc   2280
tgatccacac gtctgttcca gcagagccgc tgcctccgta ttaatttta tgacctgggc    2340
tttgaggaga ggcatctcgg ttgcttgaaa atgtgtttta atcctgtgtt gacagtattc   2400
cctactgacc gtgctgtgcg ccttctcgct tgcagctgca gggtaatata tttggaagct   2460
ttgatgagag cctgctggca cgcgccgaag ctctggcggc ggtggatatc gtctcccacg   2520
gcaagaacca tccgttcaag cccgacgcca cctaccatac catgagcagc gtgccctgca   2580
cgtccacttc gtccaccgtg cccatctccc acccagctgc gctcacctca cccctcacc    2640
acgccgtgca ccagggcctc gaaggcgacc tgctggagca catctcgccc acgctgagtg   2700
tgagcggcct gggcgctccg gaacactcgg tgatgcccgc acagatccat ccacaccacc   2760
tgggcgccat gggccacctg caccaggcca tgggcatgag tcacccgcac accgtggccc   2820
ctcatagcgc catgcctgca tgcctcagcg acgtggagtc agaccgcgc gagctggaag   2880
ccttcgccga gcgcttcaag cagcggcgca tcaagctggg ggtgacccag gcggacgtgg   2940
gcgcggctct ggctaatctc aagatccccg gcgtgggctc gctgagccaa agcaccatct   3000
gcaggttcga gtctctcact ctctcgcaca acaacatgat cgctctcaag ccggtgctcc   3060
aggcctggtt ggaggaggcc gaggccgcct accgagagaa gaacagcaag ccagagctct   3120
tcaacggcag cgaacggaag cgcaaacgca cgtccatcgc ggcgccggag aagcgttcac   3180
tcgaggccta tttcgctatc cagccacgtc cttcatctga gaagatcgcg gccatcgctg   3240
```

| agaaactgga ccttaaaaag aacgtggtga gagtctggtt ctgcaaccag agacagaaac | 3300 |
| agaaacgaat gaagtattcg gctgtccact ga | 3332 |

<210> SEQ ID NO 7
<211> LENGTH: 3500
<212> TYPE: DNA
<213> ORGANISM: Homo sapiens

<400> SEQUENCE: 7

| taccatagaa gggcttcagg aaatggtgaa cagcctgaga ttgatgtaaa gtgtgtgtgt | 60 |
| gtgtgtctgc gtgtgtgtct gtgtgtgtgt gcctgtgtgt gtgtgtgtgt ctgtctgtct | 120 |
| atggaggaga ccacagcttt catcaaattc tcatgtcttt tggttatggg gcctgctctt | 180 |
| cctttcactt cattaagtcg agtggggctc ttctaaaccc attcttatgt gctaggggct | 240 |
| agagatggga atgagagaga gtaggtagaa gacaagggaa ctaactctat acaaggcctt | 300 |
| ctattgagtc aatataagtg aaaggcttag agagtgtcca acctgcatca ggaccaataa | 360 |
| atattagctc ttattattat tattacacta tgccaaagca cttcaagttt tctcaacctc | 420 |
| acaacaaccc cacaagttca gcataagtct catattccat taggttgaac aactaaccca | 480 |
| gggtcacaca gccagtggtg gagttcagaa ctatctaatt ccaagcttag attcttcttt | 540 |
| tccaccctgt ggcctgaatt actggccaga cttttcagtct ggaggcagcc tctctgtcta | 600 |
| cccttcaggc tttcacatct aaatcccaag ggtcttgctc tttccctgag tctgtccatc | 660 |
| agaactggca tgaggcctaa aaatgagccg tttcaagccc aggcatcatc tactcactta | 720 |
| cataacaaaa cctagtcat cccactgaga ttccacactc aaagccaatt tctctcacag | 780 |
| ggcatcgaat gctagttaaa gatataaaat cacgcttatc acaattaact cccttgcctt | 840 |
| tatgatgcag ccaagtcaaa gcccaaacag gaataaattt ttctagtag ccacaaatca | 900 |
| gaggagtgag aaagctctat gccaaatcta ccattttctg atttcaaaat ccatgctaaa | 960 |
| aactgcagtt aaacatcagc taccaaaaca cccttctatc aaataagaat catggtgatt | 1020 |
| gcatgaattg agcactttct atgtacttgc tctttacgtg ttatttctat gcctcagaag | 1080 |
| agccaagcag gccagataga tgttactgct tgagaggcta agcaagtccc ataaggtcac | 1140 |
| acacacagtg aggagcagaa cctggactca aacccaggcc tatctgatga cagcaacagt | 1200 |
| gctgctaacc atgcccttcc ccccagctct ctacagtcaa tgtgattcat ggcacccagg | 1260 |
| accaacaccg gctcttggct ttcccacaaa ccacttccct gaaatctgga caacttcttg | 1320 |
| ggaggaggag tcatgggaac aggacagatg aactccaaaa tagaagatcg ggtgagaggt | 1380 |
| ccggctctgc tacttctgta gctctgtcac cacgggcaga tcacttaact ttccaaggcc | 1440 |
| tcagtttcct cgcctatgca atggagatga ccgtgaatgc cccaaattgc gctgatctag | 1500 |
| tagagaagag gagctaaggc tcaggggctt tccagacgtg agttatcttt acctttcctt | 1560 |
| gactagctaa ttcaagacaa ctaggtagaa gcccttctc agcctcccct cttcgctcat | 1620 |
| ctttcgagtt cttggccacc ccagttcaaa caccagcacc attgccctcc tctcaggtgg | 1680 |
| ctgctgctta atttcccctc cactttagta gttcttctct tgcctcgcta gaaggactgg | 1740 |
| tgttgggtgc ttggaattct ggctattttc ctcctgccgt tccgactcgg caccagagtc | 1800 |
| tgtctctact gagaacgcag cgcgtcaggg ccgagctctt cactggcctg ctccgcgctc | 1860 |
| ttcaatgcca gcgccaggcg ctcaccctgc agagcgtccc gcctctcaaa gagggggtgtg | 1920 |
| acccgcgagt ttagatagga ggttcctgcc gtggggaaca ccccgccgcc ctcggagctt | 1980 |
| tttctgtggc gcagcttctc cgcccgagcc gcgcgcggag ctgccggggg ctccttagca | 2040 |

```
cccgggcgcc ggggccctcg cccttccgca gccttcactc cagccctctg ctcccgcacg    2100
ccatgaagtc gccgttctac cgctgccaga acaccaccct gtggaaaaa ggcaactcgg    2160 cggtgatggg cggggtgctc ttcagcaccg gcctcctggg caacctgctg gccctggggc    2220
tgctggcgcg ctcggggctg gggtggtgct cgcggcgtcc actgcccccg ctgccctcgg    2280
tcttctacat gctggtgtgt ggcctgacgg tcaccgactt gctgggcaag tgcctcctaa    2340
gcccggtggt gctggctgcc tacgctcaga accggagtct gcgggtgctt gcgcccgcat    2400
tggacaactc gttgtgccaa gccttcgcct tcttcatgtc cttctttggg ctctcctcga    2460
cactgcaact cctggccatg gcactggagt gctggctctc cctagggcac cctttcttct    2520
accgacggca catcaccctg cgcctgggcg cactggtggc cccggtggtg agcgccttct    2580
ccctggcttt ctgcgcgcta cctttcatgg gcttcgggaa gttcgtgcag tactgccccg    2640
gcacctggtg ctttatccag atggtccacg aggagggctc gctgtcggtg ctggggtact    2700
ctgtgctcta ctccagcctc atggcgctgc tggtcctcgc caccgtgctg tgcaacctcg    2760
gcgccatgcg caacctctat gcgatgcacc ggcggctgca gcggcacccg cgctcctgca    2820
ccagggactg tgccgagccg cgcgcggacg ggagggaagc gtcccctcag cccctggagg    2880
agctggatca cctcctgctg ctggcgctga tgaccgtgct cttcactatg tgttctctgc    2940
ccgtaattgt gagtccccgg gccccgaggc agcaggcac tgagactgtc cggccgcgga    3000
tgcggggcgg gaagggtgga gcggatcggg atggacgcgg cgccaggcga gctgcgccct    3060
gggccaggaa ggtttgctgc tgagttcccc aaattggatt ccttccacag ccccgagata    3120
taactcagtt tgcggagcga aatgagggaa agttagagaa aggaagggaa aggctgagcc    3180
cggcggtgtc tccctagccc agcaaaaccc tctccatgtg gcagaactcc ctcctctctg    3240
cttccttctg gggagatctc gaggtcattt ttgcgcctta ggaggagcag aacttagttt    3300
ctccttggca acaggagtct tctacttccc gacggctggg tgatgtttta ttttgttaga    3360
cctgctcatg acttcagtgg tatcagaaat gggcgaatgg cgtctgggac gatcttctcc    3420
ccggtgttgg catagaaagg gaaaagagg tttaagccag ccagagtgat ttgcagatgc    3480
atagttttaa ttttgaaaaa                                              3500

<210> SEQ ID NO 8
<211> LENGTH: 3500
<212> TYPE: DNA
<213> ORGANISM: Homo sapiens

<400> SEQUENCE: 8
ttaagagaaa attctgcttt gagagctttg aaaatatttt attattatcc agaaaagtta    60
gaaaagatct caaaaaaaaa aaaaaaaaa acagcaaaaa acaaggtact acggggttaa    120
tttgtagatt gctctctctc ctcctatagt tttgttgctt atttaatcat ttgcaatgtg    180
cttttgcttt atactgaagc ccatttttt ttcagaaaaa ataaagcttt aaagtacat    240 catcatttaa atttgtctaa aatcaaccgc tttcaaaact accaactaga agtaacacct    300
ctctatgatt tctttatgca gatttaattt ttttcttgt ttgaatctta gagacccagg    360
aactagaaac actttcttaa cttgtcccct agccaaggct tcacagatac ttgcagaatt    420
aaagataagt tggcttaaaa caattgtgta agagttcttt tgagaaaaag caatgccaga    480
gaaactgaag gccaggagtt tgcaaaagtt ttgtattttt atggatgcca ctaataagca    540
agactggaca gacggtcttg ttgttgtagt atcacactca aagcagcagc attttacttc    600
```

-continued

```
tcagattcca ggtgtaagct ctactttttt atcacgcctt cataataaag aaaatctgtt       660
ctggagattc gtatattgat ttctttgcaa agttatctct aattatgcag gaatggctgt       720
tagttgccct caaaaaccaa cacaaataca caaacacaac agcctggctt agtgattatt       780
aagagctgca agtctgaagg cggactgctg ggtgtgaatt ccaccttctc aacgctgtag       840
tctccagcaa gttccttaac ttctctgcct ccgtttcctt tcctgtaaga tagagtctac       900
ctcagggtta atatgaggat atgcttcttt gctaatgctg gagggcgcta ggaatagcag       960
tggcaggctg tgtcatttct cagtgttgta taacggcttg ttttaaaagt cccactgaaa      1020
actttttttt tttccagatc gaaacacaag tttaatagtc attcagattt cattccagtc      1080
taaagaaact tatagaaatc taattatctg ccagaataac cgctttaaac tgactgtaag      1140
aaccacagtt actttgcagc taaaacagat tgttctcttc ccccaaacaa actcggacat      1200
ttagacaaat attgctgctg tctttacatt ttagaaatca gtattaaggc tcacctgtta      1260
ctgaacacat acgagaaaca gttttgttat gcgtatctta tatacatcat gtatacattt      1320
tcgtactttc acatgatgtg tataataaga tacacataaa aactggttgg cttgtcatga      1380
gtaaatgctt tattctttag agtgaaggaa tattggatac agaacgtcgt tccatattta      1440
atcttgcttt agaaaattag gatttatctt ggacacagca ttttgaatat aacacaggca      1500
agttgagtcc tgggggaaaa attgtatttt taaatttatt atcaacggtg tctttcgcat      1560
ttgagaaaac acatttgaag atgcccatgc agttccttgg aagtaaacta ggtcacccac      1620
cactgaaaca ccctcggctt ctgcaaaaag atgtgcttta aagagaatag aatggacgct      1680
cggtatgttc atctaaacga ccttgggcaa gtacgtcgat ccaaggtac aatcagccct       1740 cccagacggc ttttcgagtc tccctaaccc cggtgggaga ggacgcggcg ccagagccca      1800
gctccggcta gttttcccgg gggcaggtgt agccttgggc gcggggccgg gggaggggca      1860
aggggcgggc gtggggttgg actgggacgt gggactcgga ccacggcctg ggcgtgggcc      1920
taacgacgcg ggaccggccc gccctcgccg ctccattggc cacatctgtg cagaaaaggc      1980
cccgcggccc aggggcgccc gcagtgtcac taggccggct ggggcccctg ggtacgctgt      2040
agaccagacc gcgacaggcc agaacacggg cggcggcttc gggccgggag acccgcgcag      2100
ccctcggggc atctcagtgc ctcactcccc accccctccc ccgggtcggg ggaggcggcg      2160 cgtccgcgg agggttgagg ggagcggggc aggcctggag cgccatgagc agcccggatg       2220
cgggatacgc cagtgacgac cagagccaga cccagagcgc gctgcccgcg gtgatggccg      2280
ggctgggccc ctgcccctgg gccgagtcgc tgagccccat cggggacatg aaggtgaagg      2340
gcgaggcgcc ggcgaacagc ggagcaccgg ccggggccgc gggccgagcc aagggcgagt      2400
cccgtatccg gcggccgatg aacgctttca tggtgtgggc taaggacgag cgcaagcggc      2460
tggcgcagca gaatccagac ctgcacaacg ccgagttgag caagatgctg ggtgagtccg      2520
agtcgcagac ccaggcggcc gggcgcgctg gcgcgaatcg ctaggccgat ttcttaaacc      2580
ccaaactgtt ctttgcgagc ctgacgccca aaaccagggg tgtgtagcgg ccacgtcctt      2640
tcttaaggct ctgggttccc ttcccgcttc ccgccctccg accctccaaa gcagctttcc      2700
gccttgctct ccggctcccg gattcccag gtggccgggg gcgcgggtcc aacgctctg       2760 ggaaggcgac ttcccggcac ctccgggcgg cgcgagagca cccttggccc tgaactgggc      2820
cggttgtgtc catccctcga ccccttccct agttaggtgt cctttctgt ttttcgaacg       2880 accgggtgat gggtgagcgg aaagccgctt ccaggagacc aaaagaaagg ggtgccttta      2940
gaggacgggt gttccccaag ggctcggact caggagtccc agatctccct ctttaacttc      3000
```

| | |
|---|---|
| accccggttg cgcaattcaa agtctgaggg gggaggtgcg tccaggtggg gccaggtggg | 3060 |
| gcctggagcg ggagcgcagc cgataagccc tgcgcccctc tcccccttcc ttccactgtg | 3120 |
| caggcaagtc gtggaaggcg ctgacgctgg cggagaagcg gcccttcgtg gaggaggcag | 3180 |
| agcggctgcg cgtgcagcac atgcaggacc accccaacta caagtaccgg ccgcggcggc | 3240 |
| gcaagcaggt gaagcggctg aagcgggtgg agggcggctt cctgcacggc ctggctgagc | 3300 |
| cgcaggcggc cgcgctgggc cccgaggcg gccgcgtggc catggacggc ctgggcctcc | 3360 |
| agttccccga gcagggcttc cccgccggcc cgccgctgct gcctccgcac atgggcggcc | 3420 |
| actaccgcga ctgccagagt ctgggcgcgc ctccgctcga cggctacccg ttgcccacgc | 3480 |
| ccgacacgtc cccgctggac | 3500 |

<210> SEQ ID NO 9
<211> LENGTH: 3500
<212> TYPE: DNA
<213> ORGANISM: Homo sapiens

<400> SEQUENCE: 9

| | |
|---|---|
| tgatccctat gactcccctc tgtacaatct ttcctcctgt tctcattgct accttccaat | 60 |
| ctcctctttc atttcttcaa ctcttctttc ttgaaggaac catcccatgt ggcaactcag | 120 |
| tttctacctt ccaatgatg attgccagtc ttcactctct cctaaactct aggcttgcat | 180 |
| ttctaagtgt tattagggtg tgagcacata tgacccaggt aacgttttga aacgtttgtg | 240 |
| cctttcactt ctttcttatt ccattggttg caatcttgtc acttaatact tgaaatgttt | 300 |
| ttcaaatttg gatgtttcta gcaatcagct aatgcctttg gcctggttta ggccttcatc | 360 |
| atctcttgcc tggtttatca aagtcatttt ttaactgaac ttgttgcttt cagttcctct | 420 |
| ctgacatgat ggcattaggg taatatttcc atgtgcttca acacacatac cttctcacca | 480 |
| ttactatatg tccccccgc cacccccccc cagcatcaca ctatctctgg tgtcaccttc | 540 |
| tctgttcatg gcctttttct tcttctctag gggttccccc ctttgaagaa acagcatctg | 600 |
| ctcaacctcc cctacaggct cccttaaagc tggtttctcc tccctctgtt tgtctctttg | 660 |
| caactctctg gaggcatctt tacctttaca actttgcatt ttctctgcta ttcccatgta | 720 |
| agttccctga aacccctagta ccattcacag caggatttca aaggttgcct gttgcgtgag | 780 |
| cattctatag gatcccaaat tatctttctg tgcaaatatg aattgttgtg atatgtccgt | 840 |
| agagacggca caacctcatg gctaagaatg atagttacca gttctagaga tcctactcta | 900 |
| attgctctag agtgggggcc tgaacaccag tattacaaaa aagacaaaag aaaaagaagg | 960 |
| aaaaagaaa aagaaagag agaaaatcaa agctaccttc atcatgtatg aatttgagca | 1020 |
| agtaacacct ttgtgagtcc ccaggcccca gtttctcatt ggtaaaatga ggataacaat | 1080 |
| tacacagacc ttgttgggct atgtacagaa ttaaatgaga ttatgtacct aaaaggcttg | 1140 |
| tggcacagta acacacacac acacacacac acacacacac acccagag tacttcgtgg | 1200 |
| ttatttctag gctttactgc ttgaaaggct gaaaagatgg gtggatgaga ggtgccctga | 1260 |
| ggttccttcc aactctccaa gattctgtga tactcctcct tgggtgctga agacactttg | 1320 |
| gcaatgtttg gatttccaaa cggttgctta gaaaactaag ggaccacga agcccaggta | 1380 |
| agcctcaggg tctttcccag gaatcgttta tttatttgat cttagttctg acctagagcc | 1440 |
| tccaccttct ccatccaaat caccacagtg gtcgaaaagg gcctgtgctt gggaaatcct | 1500 |
| tcctttgttg gcgaatcttg gacccaaacc ctgcatttgg gcatctgaca cccataggcc | 1560 |

```
catggttcaa acccaggcgg ctctttccaa gttcgaagca gggactcggt tctgcgcatc    1620
tggcgggtgt gcccagattg taaccttcgc actaggcatc caagaacgtg ctttggacac    1680
actcggcggt gggagcgggt gcttggtttg catcagggat gaggggtgga gtagcgaaag    1740
cgcccggagc gcgcactcac tcacactccc caagccaggg cgcggccgct ctgggcgcga    1800
ggtcccaagc caagtctcgc gctcggccag gagccgggga gtaccccagg tccccggtct    1860
ggggccgccg ctatcctacc ctgcggcgcg cactcctgac ctggccccgc ccccggcgg     1920 ccgcgagtag cgggcggagc gcaagcagag aggcgctctg ggctgtgcgg caccgcctct    1980
cctcggtgtc tggggaggga cggagggacc gggcgggaga gagagaaagc ctgaccgacc    2040
ggctggcgaa gagctgcatg caaccggtgg gaggccgggc cggctgggtc tggggctcgg    2100
gctcaggctc gcaccgtttc tcggcaggtc cctggcggtg agcgcggacg gcccggaggc    2160
ggcggctctg agctggcagg cggagggctg tctcctgcgc ccgcctgccc ggcgcggtcc    2220
gaggatgcgg gggggcgatg cccggggcca gggacgcgct ctgtcaccag cgctgcagc    2280 tgctggccga gctctgtgcc cgtggggccc tggagcacga cagctgccag gatttcattt    2340
accacctgcg ggaccgtgcc agaccccggc tccgcgaccc aggtgagtgc cgccaccgcc    2400
gcctggaggg acctaagggc cctgggctgg gacttggggc cgcaccgggg cctgaggcag    2460
aacagcgacg cggactggga gagggcgggg ggcggccacc gagccaggag agtgatcaag    2520
aaccagcgca ctgtggcctg atgctgtaac caggcgggga cccgggcggt ggctactgca    2580
cggaggccga ctccgggtcg gctagggcag ggttggaggg accacgcccg ccacctgcgc    2640
tcccatcgcc aaggctcctg ggggcggctc cctagctccg agctacgctc tccacttccc    2700
gggctatctg cactcagagc gaggggaggc cgcggcggcc tcggagccgt gggaaggggg    2760
acgaggccga aggaaactct gggaagttgg gagttgggga cggccccggg ttggggccga    2820
atcccaccgg gtgctgctca tcctttctcc caagcgtcta gttcctttcc ttggtatggg    2880
gtgagaaggg cgggacgcga tccggcgttg ggccggggac agggtgcttc tggccttggg    2940
cagacgggcc tgaacccgtt cccggcgggt cgcacggcat ggaggtggcc tgggcctggg    3000
cgctaggctc gaccagcgac taccgccggc cacgatgggg ttcgtagact cgtcggtcct    3060
ggcttgtgca cctgtagtta ctcctagtga aagttgcaaa gctcttaact ttggaaagtt    3120
catttatttt ggcatttgac caattaaggt tggaggaggg agttttagtg gagccatttg    3180
cttttcctga ggtccctggg tctcccaggt cgtctcatcc gttactggct actggaaaat    3240
gcattccttc caatgtttgc ttgagatgtt tctcacctgg agaaatagtt ttctcgaata    3300
ttctcccaac ctaagtactt accaaaacag catattgtgg ttggattgtt aaaaatggga    3360
tgagaaaatg gcctttctct tgatattgct atgtataaat attggaaatg agctattgcc    3420
ttgcaaatta tgatgtacga attgaaaaca atttattata taaaaatcca tttatccaaa    3480
agataaatta aagaattatt                                                3500
```

<210> SEQ ID NO 10
<211> LENGTH: 28
<212> TYPE: DNA
<213> ORGANISM: Artificial Sequence
<220> FEATURE:
<223> OTHER INFORMATION: primer for detecting target gene ADRA1D
methylation status
<220> FEATURE:
<221> NAME/KEY: primer
<222> LOCATION: (1)..(28)
<223> OTHER INFORMATION: primer for detecting target gene ADRA1D
methylation status

<400> SEQUENCE: 10
ggttaggtag tttcgttttc ggatagtc                                         28

<210> SEQ ID NO 11
<211> LENGTH: 23
<212> TYPE: DNA
<213> ORGANISM: Artificial Sequence
<220> FEATURE:
<223> OTHER INFORMATION: primer for detecting target gene ADRA1D
      methylation status
<220> FEATURE:
<221> NAME/KEY: primer
<222> LOCATION: (1)..(23)
<223> OTHER INFORMATION: primer for detecting target gene ADRA1D
      methylation status

<400> SEQUENCE: 11
aaacacaaaa cgaacgaccg aca                                              23

<210> SEQ ID NO 12
<211> LENGTH: 27
<212> TYPE: DNA
<213> ORGANISM: Artificial Sequence
<220> FEATURE:
<223> OTHER INFORMATION: primer for detecting target gene AJAP1
      methylation status
<220> FEATURE:
<221> NAME/KEY: primer
<222> LOCATION: (1)..(27)
<223> OTHER INFORMATION: primer for detecting target gene AJAP1
      methylation status

<400> SEQUENCE: 12
tttggtagag tttttcgatt cggtagc                                          27

<210> SEQ ID NO 13
<211> LENGTH: 21
<212> TYPE: DNA
<213> ORGANISM: Artificial Sequence
<220> FEATURE:
<223> OTHER INFORMATION: primer for detecting target gene AJAP1
      methylation status
<220> FEATURE:
<221> NAME/KEY: primer
<222> LOCATION: (1)..(21)
<223> OTHER INFORMATION: primer for detecting target gene AJAP1
      methylation status

<400> SEQUENCE: 13
accgaaactc cgcgccgata a                                                21

<210> SEQ ID NO 14
<211> LENGTH: 25
<212> TYPE: DNA
<213> ORGANISM: Artificial Sequence
<220> FEATURE:
<223> OTHER INFORMATION: primer for detecting target gene HS3ST2
      methylation status
<220> FEATURE:
<221> NAME/KEY: primer
<222> LOCATION: (1)..(25)
<223> OTHER INFORMATION: primer for detecting target gene HS3ST2
      methylation status

<400> SEQUENCE: 14
gtaagagttt gggagcgttc gagtc                                            25

<210> SEQ ID NO 15

```
<211> LENGTH: 23
<212> TYPE: DNA
<213> ORGANISM: Artificial Sequence
<220> FEATURE:
<223> OTHER INFORMATION: primer for detecting target gene HS3ST2
      methylation status
<220> FEATURE:
<221> NAME/KEY: primer
<222> LOCATION: (1)..(23)
<223> OTHER INFORMATION: primer for detecting target gene HS3ST2
      methylation status

<400> SEQUENCE: 15
caaaaaatcc cgaaaacaac gac                                           23

<210> SEQ ID NO 16
<211> LENGTH: 27
<212> TYPE: DNA
<213> ORGANISM: Artificial Sequence
<220> FEATURE:
<223> OTHER INFORMATION: primer for detecting target gene MAGI2
      methylation status
<220> FEATURE:
<221> NAME/KEY: primer
<222> LOCATION: (1)..(27)
<223> OTHER INFORMATION: primer for detecting target gene MAGI2
      methylation status

<400> SEQUENCE: 16
cgtagagttc gagatgtggt attaggc                                       27

<210> SEQ ID NO 17
<211> LENGTH: 27
<212> TYPE: DNA
<213> ORGANISM: Artificial Sequence
<220> FEATURE:
<223> OTHER INFORMATION: primer for detecting target gene MAGI2
      methylation status
<220> FEATURE:
<221> NAME/KEY: primer
<222> LOCATION: (1)..(27)
<223> OTHER INFORMATION: primer for detecting target gene MAGI2
      methylation status

<400> SEQUENCE: 17
aaactcctat acgaaaaaaa cgcgcta                                       27

<210> SEQ ID NO 18
<211> LENGTH: 26
<212> TYPE: DNA
<213> ORGANISM: Artificial Sequence
<220> FEATURE:
<223> OTHER INFORMATION: primer for detecting target gene POU4F2
      methylation status
<220> FEATURE:
<221> NAME/KEY: primer
<222> LOCATION: (1)..(26)
<223> OTHER INFORMATION: primer for detecting target gene POU4F2
      methylation status

<400> SEQUENCE: 18
tactcccctc aaacttaaat cctttc                                        26

<210> SEQ ID NO 19
<211> LENGTH: 16
<212> TYPE: DNA
<213> ORGANISM: Artificial Sequence
<220> FEATURE:
<223> OTHER INFORMATION: primer for detecting target gene POU4F2
      methylation status
<220> FEATURE:
```

<221> NAME/KEY: primer
<222> LOCATION: (1)..(16)
<223> OTHER INFORMATION: primer for detecting target gene POU4F2
      methylation status

<400> SEQUENCE: 19
gcgggacgtt gcgaag                                                     16

<210> SEQ ID NO 20
<211> LENGTH: 19
<212> TYPE: DNA
<213> ORGANISM: Artificial Sequence
<220> FEATURE:
<223> OTHER INFORMATION: primer for detecting target gene POU4F3
      methylation status
<220> FEATURE:
<221> NAME/KEY: primer
<222> LOCATION: (1)..(19)
<223> OTHER INFORMATION: primer for detecting target gene POU4F3
      methylation status

<400> SEQUENCE: 20
agcgcgggcg ttgagtagc                                                  19

<210> SEQ ID NO 21
<211> LENGTH: 26
<212> TYPE: DNA
<213> ORGANISM: Artificial Sequence
<220> FEATURE:
<223> OTHER INFORMATION: primer for detecting target gene POU4F3
      methylation status
<220> FEATURE:
<221> NAME/KEY: primer
<222> LOCATION: (1)..(26)
<223> OTHER INFORMATION: primer for detecting target gene POU4F3
      methylation status

<400> SEQUENCE: 21
cgcgctccta acaaaataac aacgaa                                          26

<210> SEQ ID NO 22
<211> LENGTH: 25
<212> TYPE: DNA
<213> ORGANISM: Artificial Sequence
<220> FEATURE:
<223> OTHER INFORMATION: primer for detecting target gene PTGDR
      methylation status
<220> FEATURE:
<221> NAME/KEY: primer
<222> LOCATION: (1)..(25)
<223> OTHER INFORMATION: primer for detecting target gene PTGDR
      methylation status

<400> SEQUENCE: 22
ttgtttcgcg ttttttaatg ttagc                                           25

<210> SEQ ID NO 23
<211> LENGTH: 25
<212> TYPE: DNA
<213> ORGANISM: Artificial Sequence
<220> FEATURE:
<223> OTHER INFORMATION: primer for detecting target gene PTGDR
      methylation status
<220> FEATURE:
<221> NAME/KEY: primer
<222> LOCATION: (1)..(25)
<223> OTHER INFORMATION: primer for detecting target gene PTGDR
      methylation status

<400> SEQUENCE: 23
aaaaaaactc cgaaaacgac gaaat                                          25

<210> SEQ ID NO 24
<211> LENGTH: 20
<212> TYPE: DNA
<213> ORGANISM: Artificial Sequence
<220> FEATURE:
<223> OTHER INFORMATION: primer for detecting target gene SOX17
      methylation status
<220> FEATURE:
<221> NAME/KEY: primer
<222> LOCATION: (1)..(20)
<223> OTHER INFORMATION: primer for detecting target gene SOX17
      methylation status

<400> SEQUENCE: 24
ggagattcgc gtagttttcg                                                20

<210> SEQ ID NO 25
<211> LENGTH: 18
<212> TYPE: DNA
<213> ORGANISM: Artificial Sequence
<220> FEATURE:
<223> OTHER INFORMATION: primer for detecting target gene SOX17
      methylation status
<220> FEATURE:
<221> NAME/KEY: primer
<222> LOCATION: (1)..(18)
<223> OTHER INFORMATION: primer for detecting target gene SOX17
      methylation status

<400> SEQUENCE: 25
aacccgacca tcaccgcg                                                  18

<210> SEQ ID NO 26
<211> LENGTH: 25
<212> TYPE: DNA
<213> ORGANISM: Artificial Sequence
<220> FEATURE:
<223> OTHER INFORMATION: primer for detecting target gene SYT9
      methylation status
<220> FEATURE:
<221> NAME/KEY: primer
<222> LOCATION: (1)..(25)
<223> OTHER INFORMATION: primer for detecting target gene SYT9
      methylation status

<400> SEQUENCE: 26
tggggtcgtc gttattttat tttgc                                          25

<210> SEQ ID NO 27
<211> LENGTH: 18
<212> TYPE: DNA
<213> ORGANISM: Artificial Sequence
<220> FEATURE:
<223> OTHER INFORMATION: primer for detecting target gene SYT9
      methylation status
<220> FEATURE:
<221> NAME/KEY: primer
<222> LOCATION: (1)..(18)
<223> OTHER INFORMATION: primer for detecting target gene SYT9
      methylation status

<400> SEQUENCE: 27
ccgcccgatc cctccgtc                                                  18